United States Patent
Griessmann et al.

(10) Patent No.: US 10,159,776 B2
(45) Date of Patent: Dec. 25, 2018

(54) DIALYSIS MACHINE

(75) Inventors: Erik Griessmann, Schweinfurt (DE);
Frank Hedmann, Volkach (DE);
Joachim Wich-Heiter, Kuernach (DE)

(73) Assignee: PRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 1077 days.

(21) Appl. No.: 13/534,514

(22) Filed: Jun. 27, 2012

(65) Prior Publication Data
US 2013/0006171 A1 Jan. 3, 2013

Related U.S. Application Data

(60) Provisional application No. 61/502,467, filed on Jun. 29, 2011.

(30) Foreign Application Priority Data

Jun. 29, 2011 (DE) .......................... 10 2011 105 916

(51) Int. Cl.
*A61M 1/16* (2006.01)
*A61M 1/28* (2006.01)

(52) U.S. Cl.
CPC .............. *A61M 1/16* (2013.01); *A61M 1/166* (2014.02); *A61M 1/28* (2013.01); *A61M 1/282* (2014.02); *A61M 2205/12* (2013.01); *A61M 2205/3331* (2013.01); *A61M 2205/3368* (2013.01); *A61M 2205/50* (2013.01)

(58) Field of Classification Search
CPC .......... A61M 1/16; A61M 1/28; A61M 1/282; A61M 1/166; A61M 2205/50; A61M 2205/3368; A61M 2205/3331; A61M 2205/12
See application file for complete search history.

(56) References Cited

U.S. PATENT DOCUMENTS

| 5,634,896 A | 6/1997 | Bryant et al. |
| 2007/0138069 A1 | 6/2007 | Roncadi et al. |
| 2008/0161751 A1* | 7/2008 | Plahey .................... A61M 1/28 604/29 |

(Continued)

FOREIGN PATENT DOCUMENTS

| CN | 101247840 | 8/2008 |
| CN | 101269247 | 9/2008 |

(Continued)

OTHER PUBLICATIONS

Hörl, W.H. and Wanner, C.; "Dialysis Procedures in the Clinic and Practice", $6^{th}$ Ed., pp. 99-102.

*Primary Examiner* — Lauren P Farrar
(74) *Attorney, Agent, or Firm* — Jacobson Holman, PLLC.

(57) ABSTRACT

The present invention relates to a dialysis machine, in particular a peritoneal dialysis machine, wherein a dialysis treatment, in particular a peritoneal dialysis treatment, can be carried out by means of the dialysis machine in accordance with predefined and/or inputtable treatment parameters and wherein the dialysis machine has at least one setting means by means of which at least one treatment parameter can be set dynamically and/or during the treatment operation of the dialysis machine. The present invention furthermore relates to a method of operating a dialysis machine.

26 Claims, 12 Drawing Sheets

(56) References Cited

U.S. PATENT DOCUMENTS

Figure 1A:
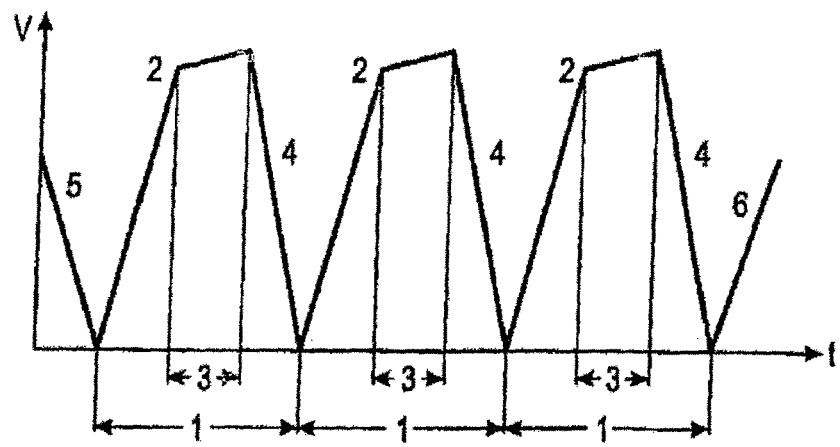

| | | | |
|---|---|---|---|
| 2008/0249377 A1 | 10/2008 | Molducci et al. | |
| 2009/0294339 A1* | 12/2009 | Biewer | A61M 1/28 210/85 |
| 2010/0010427 A1* | 1/2010 | Yu | A61M 1/28 604/29 |
| 2010/0137782 A1* | 6/2010 | Jansson | A61M 1/28 604/28 |
| 2010/0191180 A1 | 7/2010 | Childers et al. | |
| 2010/0191181 A1* | 7/2010 | Childers | A61M 1/28 604/29 |
| 2011/0077586 A1 | 3/2011 | Plahey et al. | |
| 2012/0029937 A1* | 2/2012 | Neftel | A61M 1/16 705/2 |

FOREIGN PATENT DOCUMENTS

| | | |
|---|---|---|
| CN | 10131489 | 1/2009 |
| DE | 1 964 733 | 7/1971 |
| DE | 92 03 785.2 | 6/1992 |
| JP | H09225024 | 9/1997 |
| JP | 2002510533 | 4/2002 |
| JP | 2004057248 | 2/2004 |
| JP | 2007508101 | 4/2007 |
| JP | 2009011667 | 1/2009 |
| WO | WO 99/51287 | 10/1999 |
| WO | WO 2005/035023 | 4/2005 |
| WO | WO 2006/034178 | 3/2006 |
| WO | WO 2007/091217 | 8/2007 |
| WO | WO 2009/149002 | 12/2009 |
| WO | WO 2010/108955 | 9/2010 |

\* cited by examiner

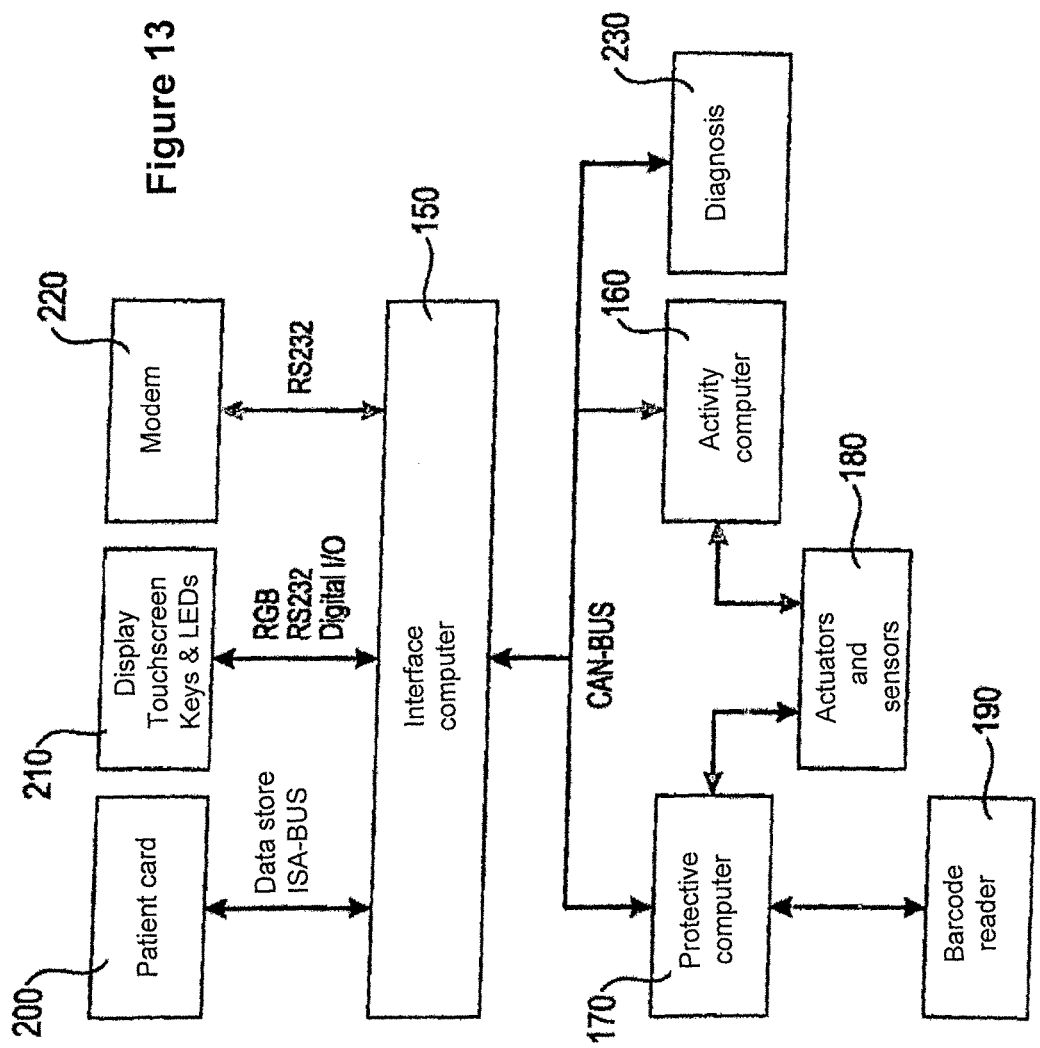

DIALYSIS MACHINE

This application claims the benefit of U.S. provisional application No. 61/502,467, filed Jun. 29, 2011, which claims the priority of German number 10 2011 105 916 . 8 filed Jun. 29, 2011, hereby incorporated by reference.

The present invention relates to a dialysis machine as well as to a method of operating a dialysis machine.

On the carrying out of peritoneal dialysis treatment, a planned treatment duration is predefined at the start of the treatment. The planned treatment duration results from the individual filling, dwell and drain phases of each cycle of peritoneal dialysis treatment.

Furthermore, a treatment volume is prescribed for the patient for the carrying out of peritoneal dialysis treatment. Which bags are to be connected to the dialysis machine then results from this. The dialysis solution can be composed of the bag content of a plurality of solutions contained in the respective bags. The bag selection with respect to the bag size takes place by the patient him or herself, with the patient only having to connect the respective bag and a sufficient nominal volume.

It must be noted that the dialysis machine has its own consumption of solution which is caused, for example, by calibration and flushing processes of the dialysis machine, with this solution consumed for this purpose then being discarded and not being used for treatment purposes. There is thus a discarding of solution on every treatment.

The available minimum treatment volume of dialysate is usually is infused periodically into the peritoneum of the patient in a plurality of part volumes, which are also called instillation volumes, and remains there for a predefined dwell time, also called a dwell phase.

Extensions to the treatment duration are, for example, perceived as disadvantageous; it is equally disadvantageous if the available dialysate volume cannot be completely utilized because e.g. the remaining residual volume is not sufficient for a proper treatment and is therefore not infused, but is rather discarded.

The actual treatment duration can be influenced by a plurality of factors, namely in particular by the actually achieved flow rates on the instillation and drain processes of the dialysate, the actually dispensed volume for instillations and the ultrafiltration volume generated by the patient and additionally removed on drain processes.

Furthermore, changes can occur with respect to the required treatment duration, namely e.g. as a consequence of a change of the course of treatment by the patient (e.g. manual draining or skipping treatment cycles), a change of parameters of the treatment prescription during the treatment (changing volumes for subsequent instillations, changing of dwell times) or by an interruption or pause of the treatment by the patient.

The available bag volume also changes in the course of the treatment to the extent that the respective solutions are already dispensed to the patient. The change in the bag volume can furthermore be due to the fact that the solution was needed for internal processes (e.g. for adjusting the pump, priming, etc.) or the solution is discarded due to alarms (e.g. fluid too hot). It is also possible that the instillation solution required for the treatment varies, for instance due to a change of the course of the treatment on the user side (e.g. manual draining or skipping of cycles) or by a change of parameters of the treatment prescription during the treatment (e.g. a change of volumes for subsequent instillations).

A peritoneal dialysis machine is known from WO 2009/149002 A2 which enables the changing of displayed treatment parameters via an input.

WO 1999/51287 A1 describes a peritoneal dialysis machine operable in TPD (tidal peritoneal dialysis) mode.

WO 2007/091217 A1 discloses a peritoneal dialysis machine which allows a changing of the dwell time of the dialysate in the patient.

WO 2005/035023 A1 relates to a peritoneal dialysis machine in which the dialysate outflow from the peritoneum of the patient is monitored by means of a sensor. In this respect, the dialysate outflow is interrupted when a threshold value is reached.

WO 2006/034178 A2 discloses a peritoneal dialysis machine in which a determination of the dialysate not yet infused takes place.

JP 2009-011667 A describes a peritoneal dialysis machine which calculates the requirement for dialysis fluid.

US 2010/0191180 A1 relates to a peritoneal dialysis machine which allows adaptations of treatment parameters.

It is therefore the object of the present invention to further develop a dialysis machine of the initially named kind in an advantageous manner, in particular such that the planned treatment duration is substantially observed and the available dialysate volume can also be used optimally.

This object is achieved in accordance with the invention by a dialysis machine having the features of claim 1. Provision is accordingly made that a dialysis machine is configured such that a dialysis treatment, in particular a peritoneal dialysis treatment, can be carried out by means of the dialysis machine in accordance with predefined and/or inputtable treatment parameters and wherein the dialysis machine has at least one setting means by means of which at least one treatment parameter can be set dynamically and/or during the treatment operation of the dialysis machine.

In particular the part volumes or individual volumes, the number of treatment cycles, the dialysate to be used and the dwell time are fixed as treatment parameters before the carrying out of the treatment and are stored as a treatment plan in the dialysis machine. The available minimum bag volume of all connected instillation solutions is known before the start of the treatment since they are identified e.g. via barcode before the connection. The properties of the solutions are available at the machine side as information or as further treatment parameters due to the identification. It is in particular a question of information with respect to the kind of solution, bag size, minimum overfill volume, nominal fill volume, glucose concentration, calcium concentration, type of bag such as double chamber bag or single chamber bag. The minimum overfill volume is in this respect the solution volume guaranteed by the manufacturer which is present in a solution bag in addition to the nominal fill volume. The instillation volume is in this respect the volume of dialysate which is infused into the patient in a treatment cycle or is provided or determined for infusion into the patient.

The advantage in particular results and it is in particular advantageously possible that the setting of the at least one treatment parameter can be automatically adapted.

Provision can furthermore be made that the treatment parameter or parameters is/are the dwell time and/or the instillation volume which can be changed during the treatment. The dwell time is in this respect the dwell time of the dialysate in the peritoneum of the patient to be treated.

It is thus advantageously possible to be able to vary the dwell time of the dialysate in the peritoneum and the dialysate volume for the filling of the peritoneum during the individual cycles of a dialysis treatment. It is in particular possible to be able to shorten the instillation volume and the dwell time under certain circumstances within a predefined tolerance framework. A utilization of the total dialysate quantity which is as ideal as possible should thus be achieved e.g. on the shortening of the instillation volume during the cycles and the treatment after the duration of the prescribed or planned treatment time can also be terminated by the shortening of the dwell time. It is in this respect ensured despite these measures that the treatment goal can be achieved on the basis of the setting possibility of the treatment parameters dwell time and/or instillation volume.

It can now in particular be achieved that the bags connected to the dialysis machine can be utilized as much as possible. It is now in particular advantageously achieved that the bag tolerances and in particular the overfill volume is used for the machine's own consumption and further advantageously that an adaptation takes place when the bag tolerances and in particular the overfill volume should not be sufficient for the machine's own consumption.

Provision can furthermore be made that the dialysis machine has a planning means for planning a course of treatment and a monitoring means for monitoring the course of treatment, wherein it can be compared by means of the setting means whether an actual course of treatment corresponds to or deviates from a planned course of treatment. The planned course of treatment can be transferred to the planning means via a patient card, for example. It is also conceivable that such a patient card is a component of the planning means.

It is furthermore possible that at least the planned treatment duration can be predefined by means of the planning means and that at least the probable treatment duration can be calculated and/or estimated with reference to the previous treatment progress by means of the monitoring means.

Provision can furthermore be made that a plurality of dwell times are provided during the total treatment duration whose lengths are predefinable and/or predefined and stored in the planning means and wherein a correction of at least one dwell time can be carried out by means of the setting means with reference to the calculation and/or estimation of the probable treatment duration by the monitoring means so that the planned treatment duration can be adhered to.

The dynamic adaptation of the dwell times before each dwell phase has the result that the dwell phases are shortened relatively uniformly. Since the generation of ultrafiltration volumes and the substance removal reduce considerably with the duration of the dwell phase, a proper treatment can be carried out despite the shortening of the dwell phase, that is in particular the treatment goal can be reached. This dynamic adaptation can be advantageously combined with a design of the dialysis machine in which it can be evaluated before the last treatment cycle whether a shortening of the dwell phase should be carried out. If the dwell phase duration is e.g. below approximately 5 minutes, the treatment cycle is not carried out or is not started on the part of the machine. This evaluation now takes place for reasons of efficiency and comfort. The inefficiency of the simple check of the last dwell phase duration is now advantageously combated in that treatment delays were already compensated via the total treatment duration or at least a part of the treatment duration. It is now particularly advantageous that an inefficient last treatment cycle is avoided due to a comparatively small dwell duration. A further efficiency increase results in that the case can now no longer occur that the last treatment cycle is omitted due to too short a dwell duration and hereby valuable dialysis solutions is discarded unused.

It is possible that the setting means has a limiting means by means of which a percentage factor can be predefined which limits the maximum possible correction of the dwell time, with the percentage factor preferably amounting to 10% of the planned dwell time.

It is furthermore conceivable that the time difference between the planned and actual treatment duration can be calculated by means of the setting means and that the calculated time difference can be deducted from the previously predefined dwell time by means of the setting means and a dwell time accordingly corrected by the calculated time difference can be set.

Provision can furthermore be made that at least one planned instillation volume, in particular all the still planned instillation volumes, of the dialysate can be predefined by means of the planning means and that at least the instantaneously available volume of dialysate can be calculated and/or estimated by means of the monitoring means.

The situation can, for example, result that the still available volume of dialysate is no longer sufficient for all instillation volumes still planned. If the planned instillation volumes are adhered to, it could thus, for example, result that a treatment cycle would have to be omitted due to a lack of volume of dialysate. It is, however, to be preferred in such a case to shorten a plurality of planned instillation volumes, in particular all instillation volumes, to be able to maintain all planned treatment cycles with now reduced instillation volumes. For, due to the concentration difference, the transfer into the dialysate of the materials or substances to be removed by means of the dialysis treatment takes place substantially more effectively at the start of a treatment cycle so that it is more advantageous to maintain all treatment cycles in order to utilize this effect of the improved substance transfer into the fresh dialysate and in return optionally to shorten the respective instillation volume of a treatment cycle.

Since the instillation volumes can advantageously be dynamically adapted by means of the setting means before each instillation, the available solution quantity which is known to the dialysis machine, as already described above with regard to the relevant details and thus also with regard to the minimum treatment volume, can be ideally consumed. It is no longer necessary to fix a safety volume for the treatment. This increases the transparency of prescription to required bags. It is thus now possible for a 15 l treatment e.g. to use either three bags @ 5 l or five bags @ 3 l, although the guaranteed minimum volume, which results from the nominal bag fill volume and the guaranteed overfill volume, of the two variants is different. A further advantage furthermore results in that, unlike a shortening of an instillation at the end of the treatment (by an alarm), the instillations are uniformly shortened. This makes possible, as already described in detail above, a more proper treatment for the patient, that is a better achievement of the treatment goal. It is furthermore no longer necessary, e.g. on post-treatments and with sleeping patients, to waken the patient by an alarm to abort the instillation due to a lack of solution.

It is furthermore possible that a correction of at least one planned installed volume and/or of all still planned instillation volumes can be carried out by means of the setting means based on the calculation and/or estimation of the monitoring means of the instantaneously available volume of dialysate.

It is conceivable that the setting means has a limiting means by means of which a percentage factor can be predefined which limits the maximum possible correction of the planned instillation volume, with the percentage factor preferably amounting to 10% of the planned instillation volume.

Provision can furthermore be made that the volume difference between the planned and the actual instillation volume or between the planned and actual instillation volumes can be calculated by means of the setting means and that the calculated instillation volume or the calculated instillation volumes can be deducted from the previously predefined instillation volume or from the previously predefined instillation volumes by means of the setting means and accordingly a corrected instillation volume or corrected instillation volumes can be set by the calculated volume difference.

The present invention furthermore relates to a method of operating a dialysis machine having the features of claim 12. Accordingly, provision is made in a method of operating a dialysis machine that a dialysis treatment, in particular a peritoneal dialysis treatment, can be carried out in accordance with predefined and/or inputtable treatment parameters, and wherein at least one treatment parameter can be set and/or is set dynamically at the machine side and/or during the treatment operation of the dialysis machine.

The method can in particular and advantageously be carried out using a dialysis machine in accordance with one of the claims 1 to 11.

The dynamic and in particular automatic setting makes it possible that the treatment can be carried out within a tolerance range. This tolerance range in this respect takes account both of the time-dependent (horizontal) aspect and the volume-dependent (vertical) aspect. The tolerance range can be adapted in a horizontal and vertical direction by the fixing of the factors for the time management and volume management. A predefined treatment is thus advantageously carried out within the predefined tolerance range.

Further details and advantages of the present invention will now be explained in more detail with reference to an embodiment shown in the drawing.

Figure 2:
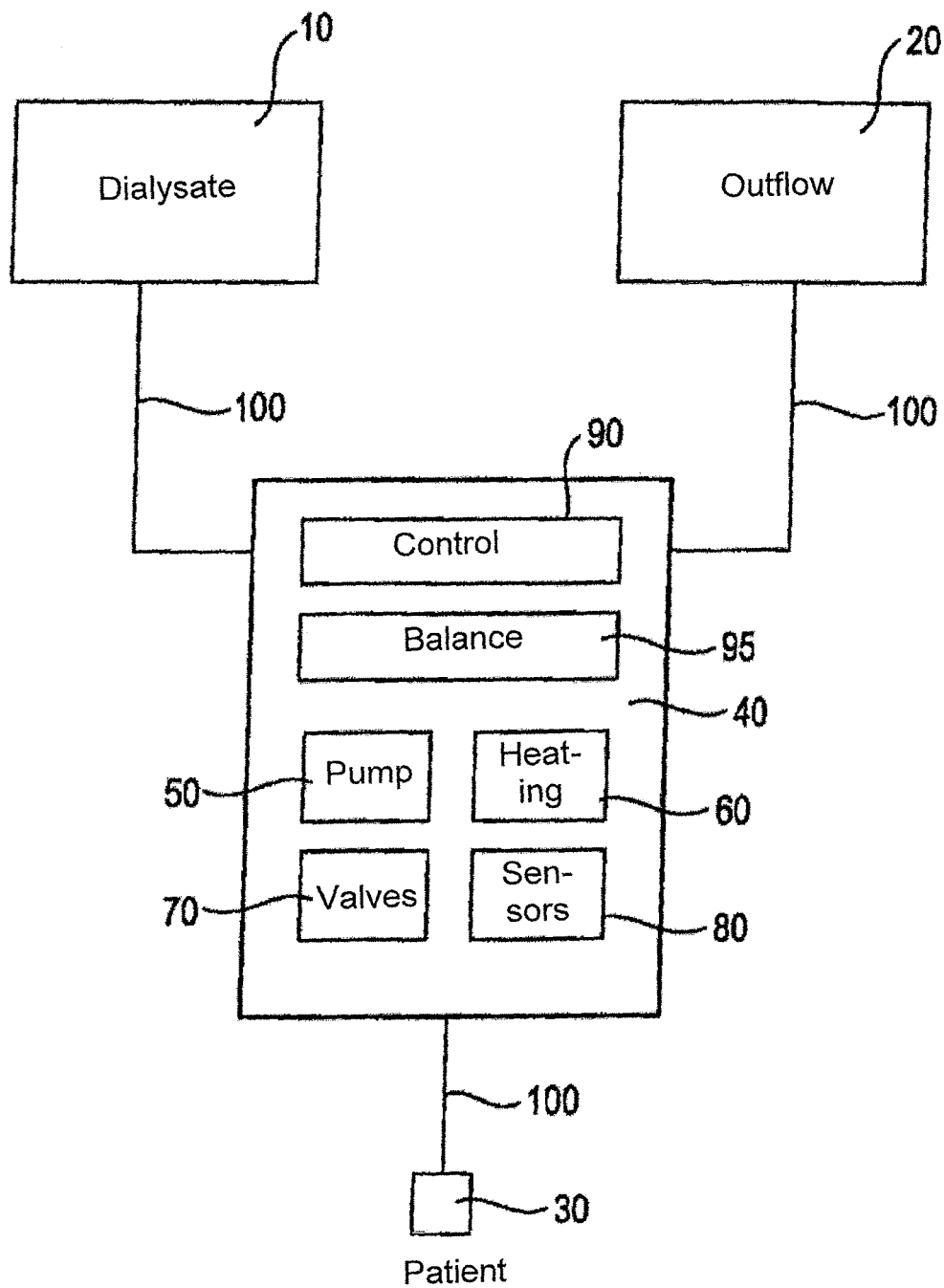
Figure 3:
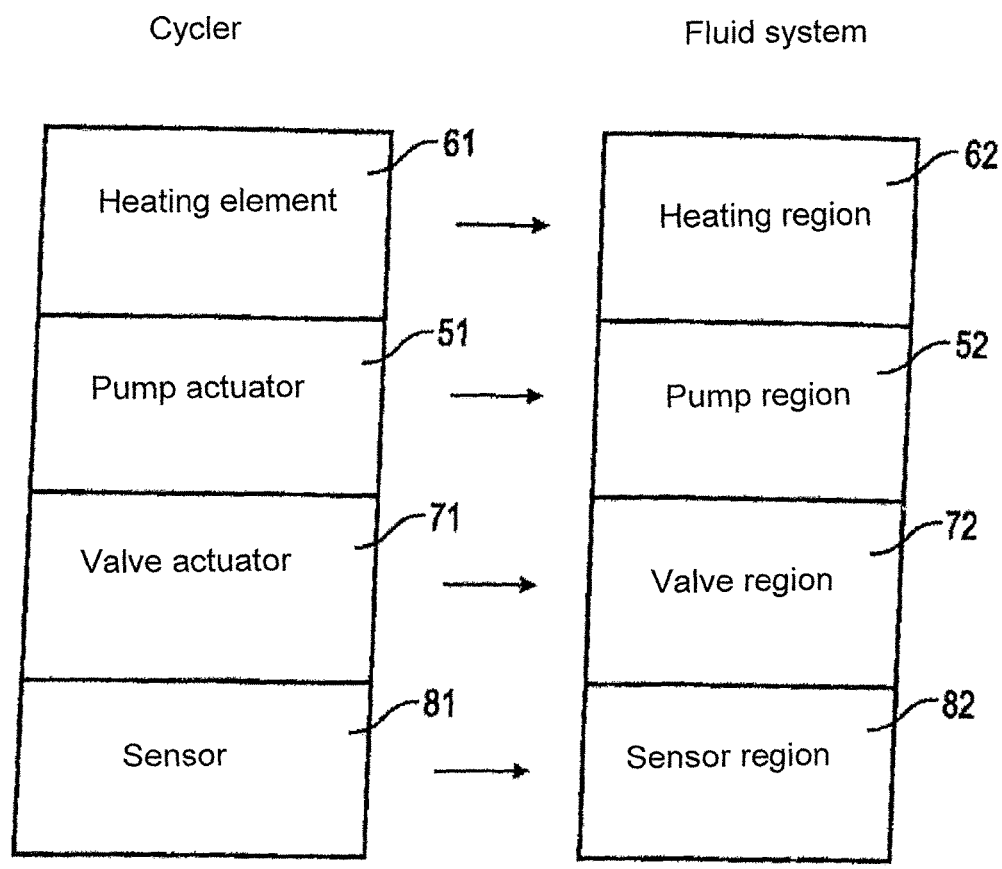
Figure 5:
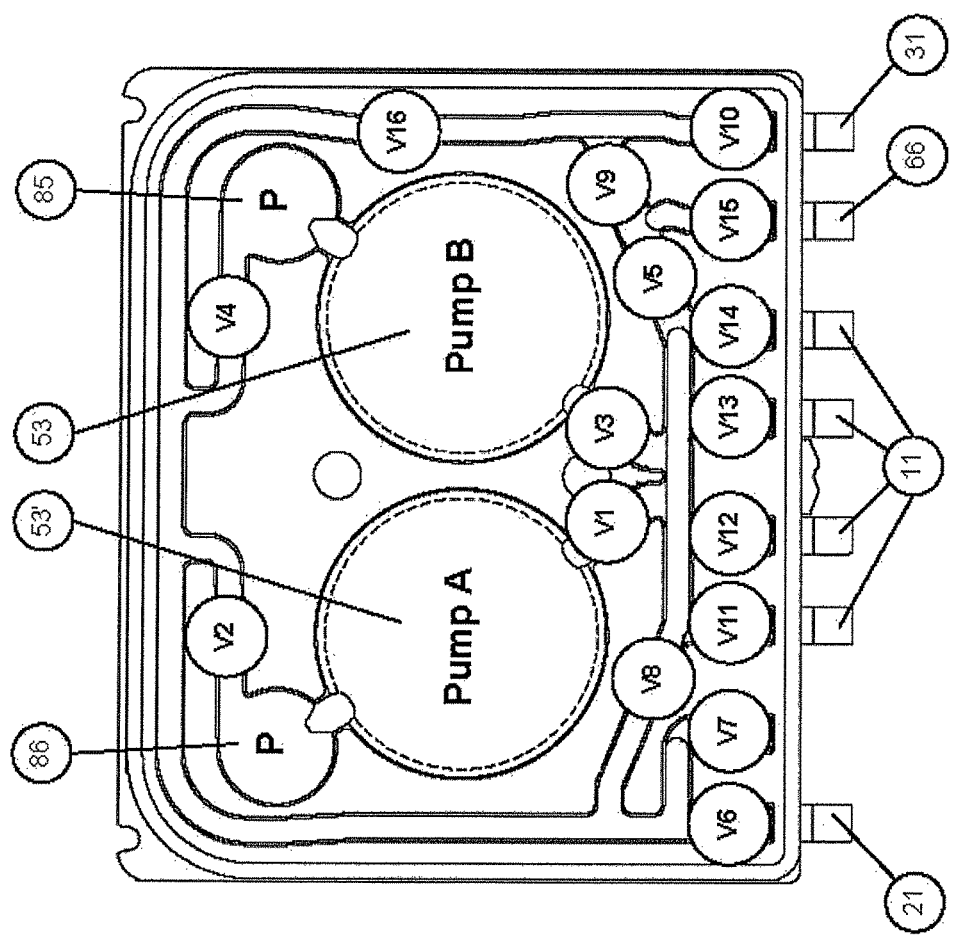
Figure 6:
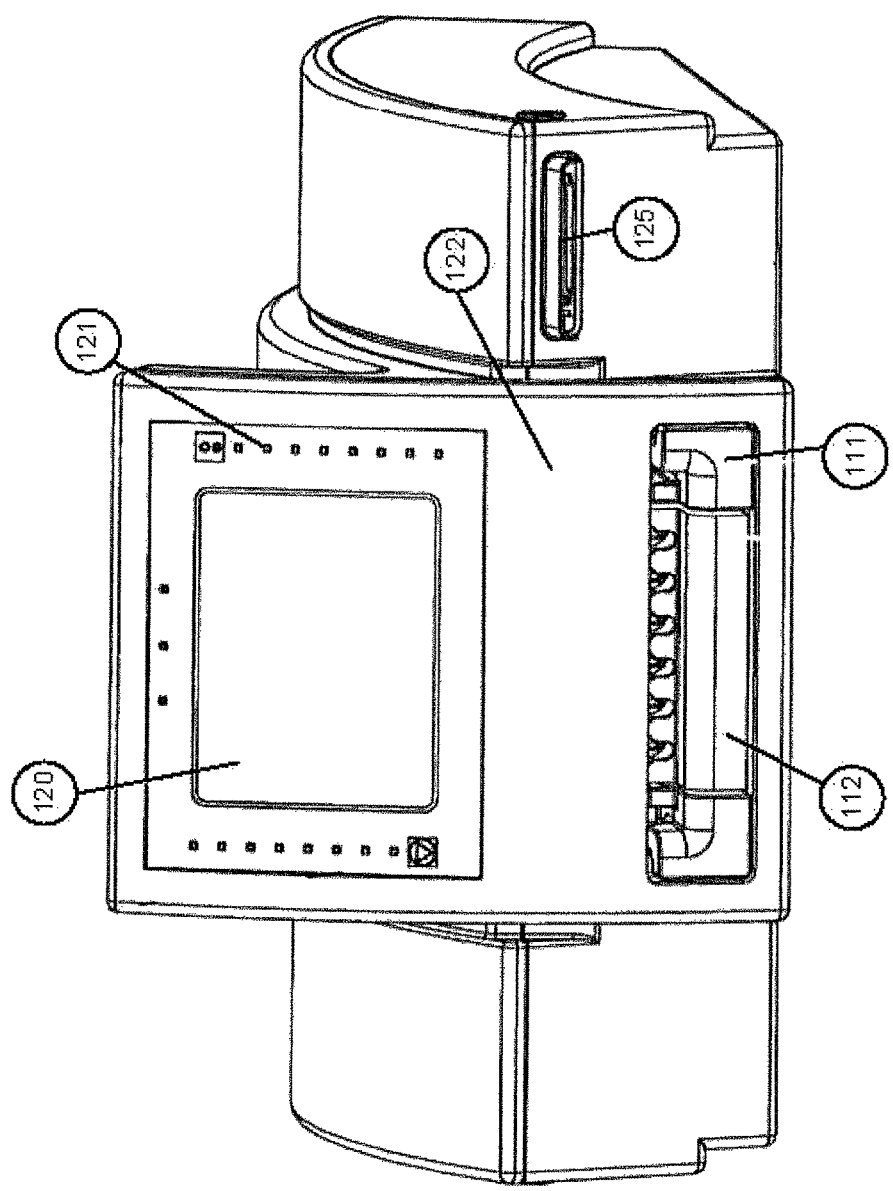
Figure 7:
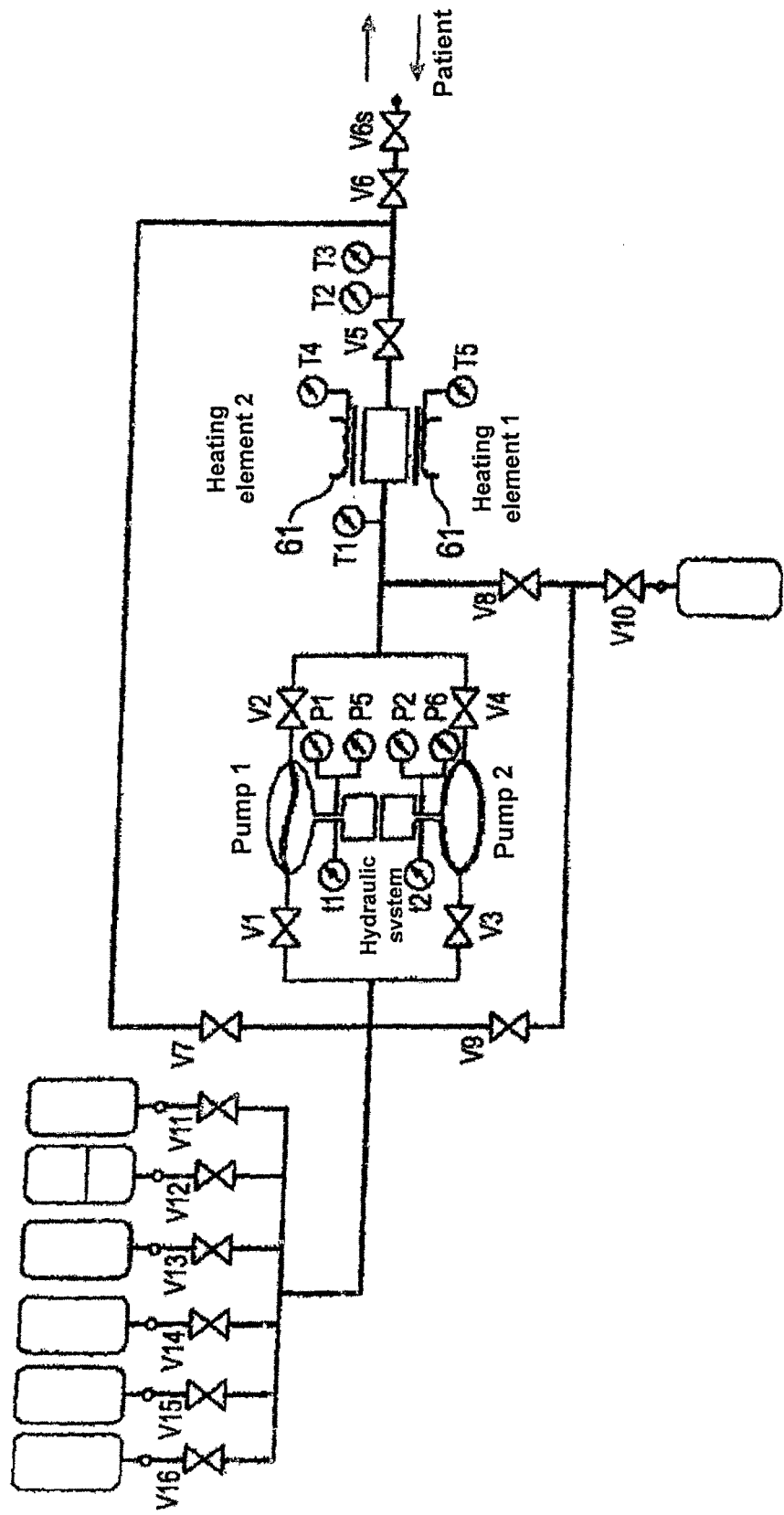
Figure 8:
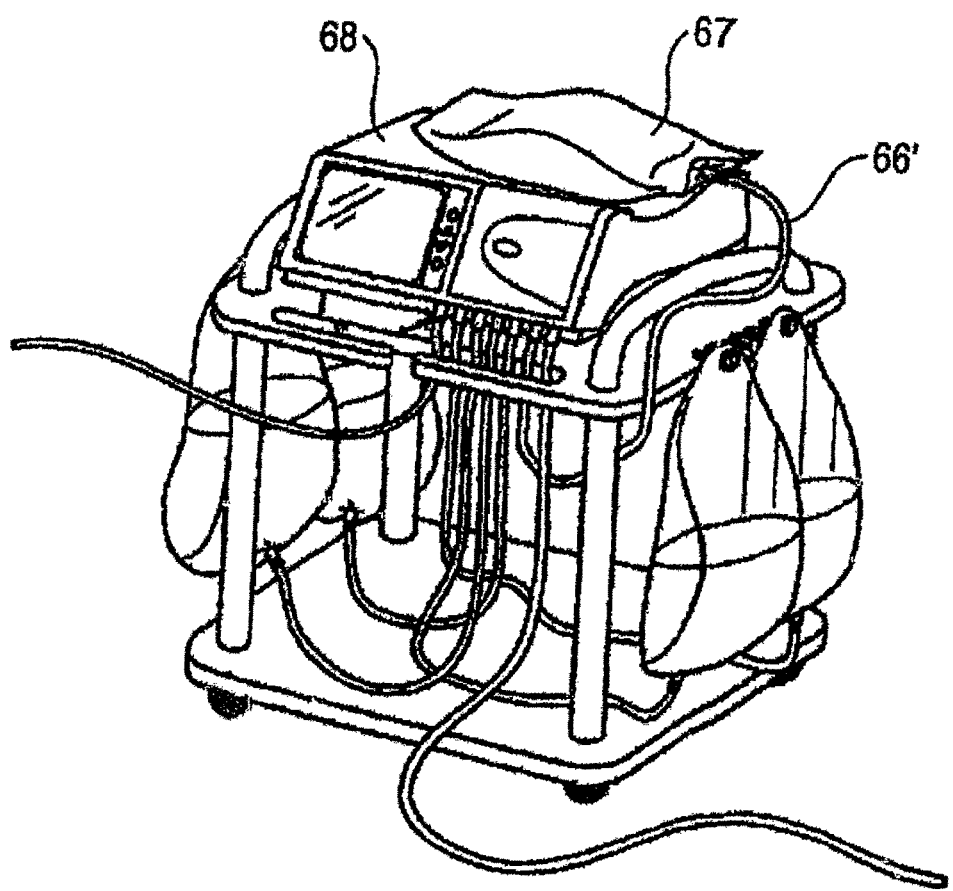
Figure 9:
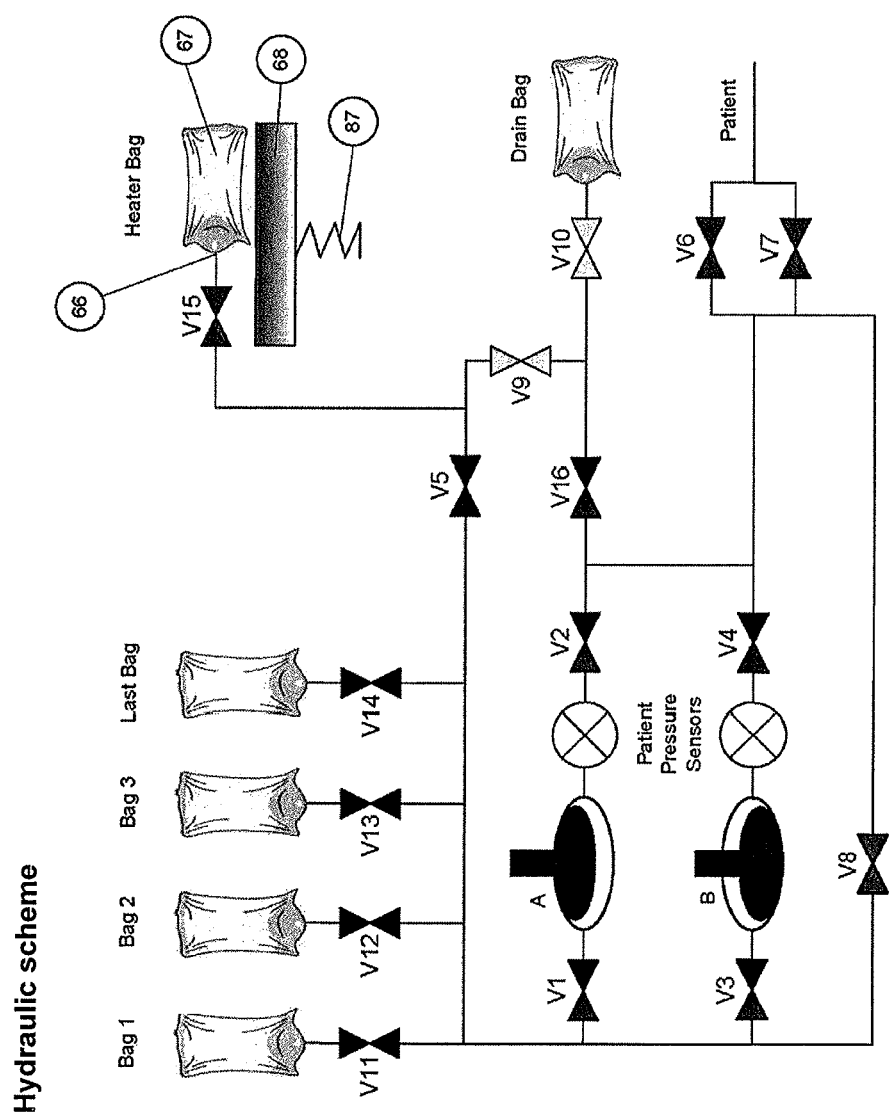
Figure 10:
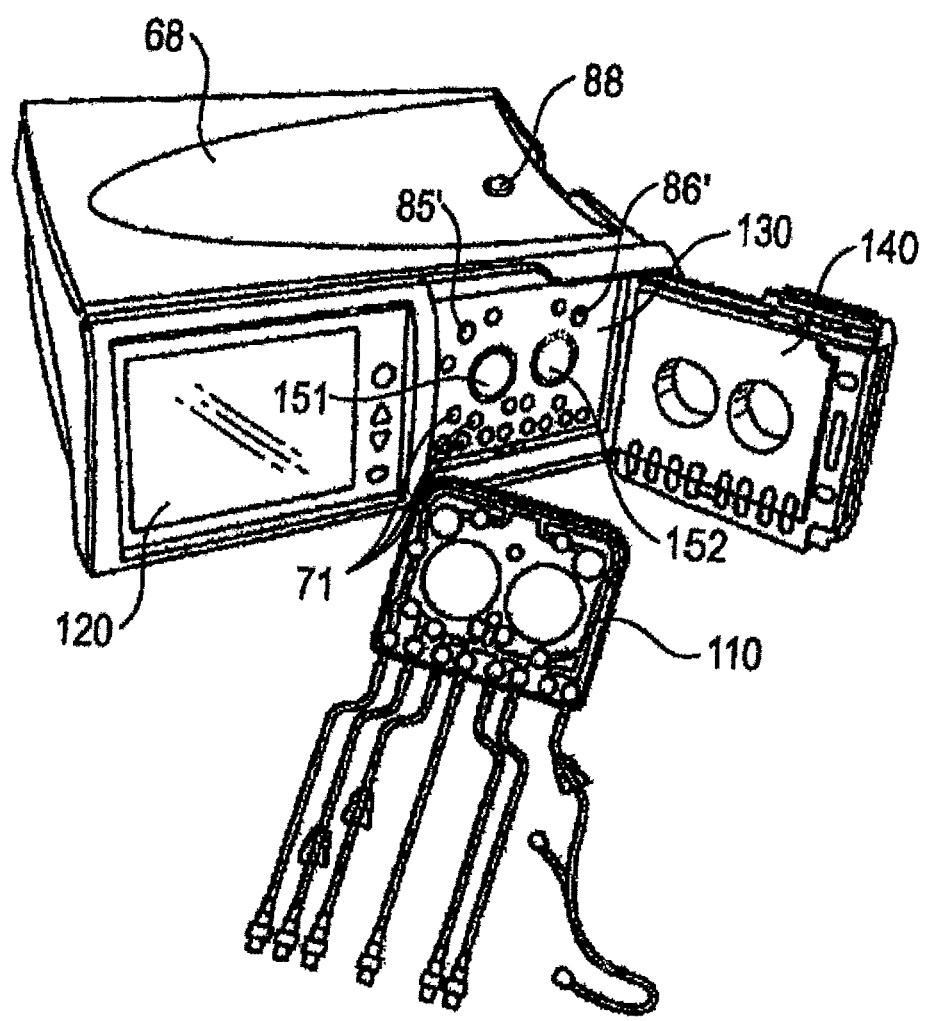
Figure 11:
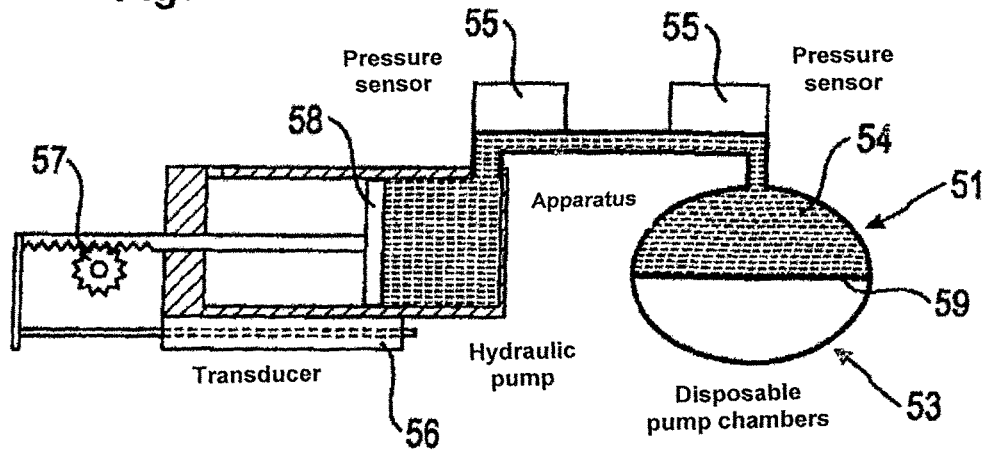

There are shown:

FIG. 1 three diagrams which show typical developments of an automatic peritoneal dialysis treatment;

FIG. 2 a schematic diagram of a peritoneal dialysis machine;

FIG. 3 a schematic diagram of the division of the peritoneal dialysis system into a dialysis machine and a fluid system;

FIG. 4 a first embodiment of a cassette;

FIG. 5 a second embodiment of a cassette;

FIG. 6 a perspective view of a first embodiment of a dialysis machine;

FIG. 7 a flowchart of a first embodiment of a peritoneal dialysis system;

FIG. 8 a perspective view of a second embodiment of a dialysis machine;

FIG. 9 a flowchart of a second embodiment of a peritoneal dialysis system;

FIG. 10 the coupling of the cassette in the second embodiment of a peritoneal dialysis system;

FIG. 11 a first embodiment of a pump actuator;

FIG. 12 the coupling of a pumping region of the cassette to a pump actuator; and FIG. 13 a schematic diagram of the design of an embodiment of a controller.

The function of a dialysis machine in which the present invention is used will first be described generally in the following. The dialysis machine in this embodiment is in this respect a peritoneal dialysis machine. The components described below can, however, also be used in the same manner or in a similar manner for a hemodialysis machine.

Peritoneal dialysis is a variant of artificial hemodialysis in which the peritoneum of the patient which has a good blood supply is used as a filter membrane natural to the body. Dialysate is introduced into the abdominal cavity via a catheter for this purpose. In accordance with the principle of osmosis, urea components of the blood now diffuse through the peritoneum into the dialysate present in the abdominal cavity. After a specific dwell time, the dialysate with the urea components is again eliminated from the abdominal cavity.

In automatic peritoneal dialysis, a dialysis machine controls and monitors the introduction of the fresh dialysate into the abdominal cavity and the elimination of the consumed dialysate. Such a dialysis machine, also called a cycler, in this respect usually fills and voids the abdominal cavity several times overnight, i.e. while the patient is asleep.

Figure 1B:
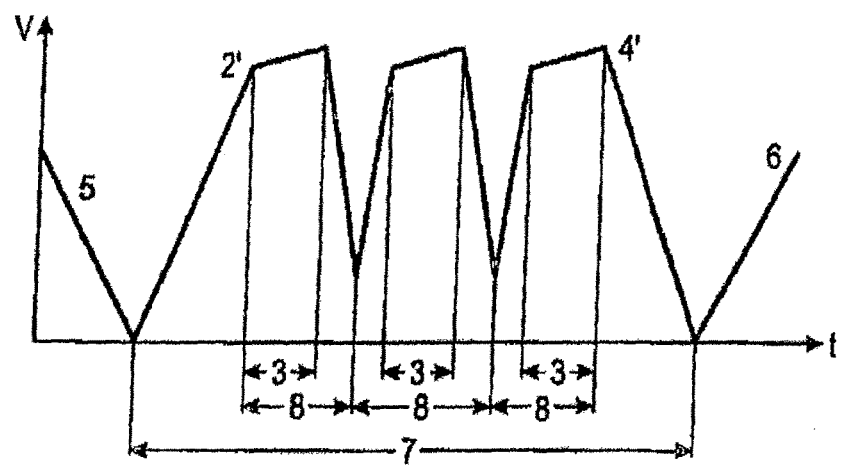
Figure 1C:
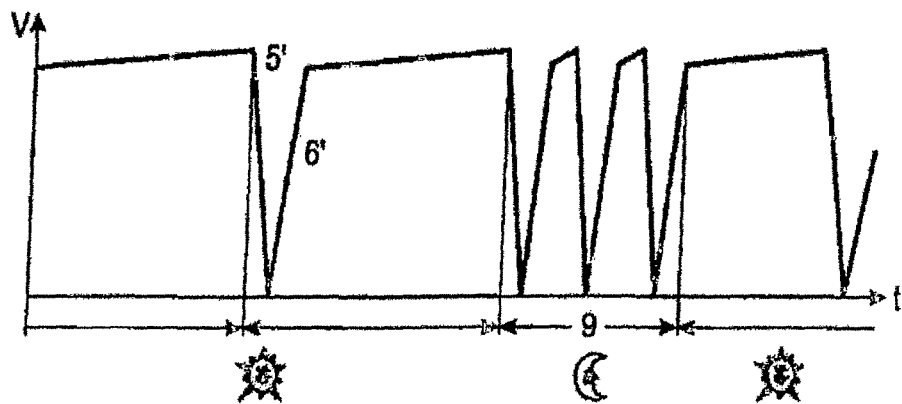

In FIGS. 1a to 1c, three different method procedures are shown such as are carried out by a dialysis machine. One of more of these process procedures is in this respect usually stored in the controller of the dialysis machine. It is usually possible in this respect to adapt the stored process procedures to the patient.

In FIGS. 1a to 1c, the dialysate quantity V respectively present in the patient's abdominal cavity is entered over the time t. In this respect, FIG. 1a shows the development of a normal automatic peritoneal dialysis treatment overnight. At the start of the treatment, an initial drain process 5 first takes place in this respect through which dialysate which was left in the abdominal cavity of the patient over the day is removed. A plurality of treatment cycles 1 then follow; in FIG. 1a, three sequential treatment cycles 1. Each treatment cycle consists of an instillation phase 2, a dwell phase 3 and a drain phase 4. In this respect, a specific volume of fresh dialysate fluid is introduced into the patient's abdominal cavity during the instillation phase 2. The maximum permitted dialysate quantity in this respect amounts to between approximately 1.5 and 3 l depending on the patient. The fresh dialysate now remains in the abdominal cavity for a specific dwell time 3. The dwell phase in this respect typically lasts some hours. The now consumed dialysate is then removed from the abdominal cavity again in the drain phase 4. A new treatment cycle then starts. The treatment is concluded with a last instillation 6 by which a specific quantity of fresh dialysate is introduced into the patient's abdominal cavity. It then remains in the patient's abdominal cavity over the day.

The individual treatment cycles 1 which take place overnight are in this respect automatically controlled by the controller of the dialysis machine. The initial drain process and the last instillation can likewise be controlled automatically by the dialysis machine. Alternatively, they are activated manually by an operator or by the patient.

A so-called tidal treatment is shown in FIG. 1b. This also starts with an initial drain process 5 and ends with a last instillation 6. A base cycle 7 is furthermore provided which is divided into a plurality of tidal cycles 8. In this respect, a base instillation phase 2' is initially provided. After the dwell time 3, however, the complete dialysate volume is no longer removed from the abdominal cavity, but rather only a certain part quantity of the dialysate present in the abdominal cavity. This is then replaced by a corresponding volume of fresh dialysate. After a further dwell cycle, a further tidal removal can take place in which the total dialysate present in the abdomen is not removed. At the end of the base cycle 7, a base drain phase 4' takes place in which the total dialysate is now removed. Only one base cycle is in this respect shown in FIG. 1b. Alternatively, however, a plurality of base cycles can also be provided.

The course of a peritoneal dialysis treatment with a so-called PD plus treatment is shown in FIG. 1c. In this respect, a conventional peritoneal dialysis treatment takes place during the night 9 which can e.g. be carried out in accordance with the FIG. 1a or 1b. An additional PD plus treatment is, however, furthermore provided during the day in which the consumed dialysate is removed in a drain phase 5' and is replaced by fresh dialysate in an instillation phase 6'. In the PD plus treatment, a normal night-time peritoneal dialysis treatment is combined with one or more additional treatment cycles during the day. The course of the night-time treatment is in this respect carried out as customary automatically by the dialysis machine. The treatment cycles during the day are likewise carried out and monitored via the machine.

The design of a typical peritoneal dialysis system is now shown schematically in FIG. 2. The peritoneal dialysis system in this respect includes a container 10 with fresh dialysate and a drain 20 for used dialysate. A connector 30 is furthermore provided which can be connected to a catheter of the patient either to introduce fresh dialysate into the abdominal cavity of the patient or to remove consumed dialysate from the abdominal cavity. The container 10 with fresh dialysate, the drain 20 for used dialysate and the connector 30 to the patient are in this respect connected to one another via fluid paths 100 and form the fluid system of the peritoneal dialysis system together with them.

A dialysis machine 40, also called a cycler, is provided for the carrying out of the peritoneal dialysis treatment. The dialysis machine 40 in this respect includes the following main components:

- A pump 50 which is used for the transport of the fluids. The pump 50 in this respect conveys the fresh dialysate from the container 10 to the connector 30. The pump 50 can furthermore transport the consumed dialysate from the connector 30 to the drain 20.
- Valves 70 which are used for the control of the fluid flows. The valves 70 open and close the fluid paths 100 in order thus to establish the corresponding fluid connections between the container 10, the connector 30 and the drain 20.
- A heating 60 which brings the fresh dialysate to a temperature of approximately 37° C. before it is supplied to the patient. Since relatively large quantities of dialysate are supplied directly into the abdominal cavity of the patient in peritoneal dialysis, the heating 60 is necessary in order not to cool the patient too much and to avoid an unpleasant feeling by dialysate which is too cold.
- Sensors 80 via which the proper procedure of the treatment can be monitored and/or controlled. Temperature sensors can in particular be used in this respect. Pressure sensors can furthermore optionally be used.

All the components of the dialysis machine 40 are in this respect controlled via a controller 90. In this respect, the controller 90 in particular controls the pump 50, the heating 60 and the valves 70 on the basis of the data of the sensors 80. The controller 90 in this respect provides the automatic procedure of the peritoneal dialysis. The controller 90 in this respect includes as an important component a balance 95 which balances the fluid quantities supplied to and removed from the patient. The balance in this respect prevents the patient from being given too much fluid or having too much fluid removed.

The balance 95 can in this respect take place solely on the basis of the control data and/or the sensor data for the pump 50. Alternatively, the balance can also take place via separately provided balancing chambers. It is equally possible to use scales for the balancing. Such scales, for example, weigh the weight of the container 10 with fresh dialysate and/or a container 20 with used dialysate.

Since the dialysate is dispensed to the patient directly into the abdominal cavity in peritoneal analysis, extreme sterility must be observed. The fluid paths or the fluid system which comes into contact with the fresh dialysate and/or the used dialysate are therefore usually designed as disposable parts. The fluid paths or the fluid system are in this respect in particular designed as plastic parts. They can thus be supplied in a sterile outer packaging and only unpacked briefly before the treatment.

In order nevertheless to enable a control of the peritoneal dialysis by the dialysis machine 40, the fluid system has to be coupled to the dialysis machine 40. In this respect, it is shown schematically in FIG. 3 how individual elements of the dialysis machine 40 are coupled to corresponding regions of the fluid system.

The dialysis machine 40 in this respect has a heating element 61. This must be coupled to a corresponding heating region 62 of the fluid system. The coupling in this respect enables the transfer of thermal energy from the heating element 61 to the dialysate present in the heating region 62.

The dialysis machine 40 furthermore has one or more pump actuators 51 which are coupled to a pump region 52 of the fluid system. The pump actuators 51 in this respect generate a pump force which is transferred to the pump region 52. The fluid present in the pump region 52 can hereby be moved along the fluid paths.

The dialysis machine furthermore has one or more valve actuators 81. They generate a closing movement which is transferred to corresponding valve regions 72 of the fluid paths. The valve regions 72 of the fluid paths can hereby be correspondingly closed or opened.

The dialysis machine furthermore has one or more sensors 81. They are coupled to a corresponding sensor region 82 of the fluid system. The sensors 81 can hereby measure specific properties of the dialysate. The temperature of the dialysate can in particular be measured hereby. Provision can furthermore be made that the pressure in the fluid system is determined.

The dialysis machine naturally optionally has further actuators and/or sensors which do not have to be coupled to the fluid paths.

The individual components of a peritoneal dialysis system should now be presented in more detail in the following with reference to embodiments.

1. Fluid System 1.1 Dialysis Container

Fresh dialysate is usually provided in plastic bags. Such plastic bags usually have two layers of plastic film which are welded to one another in a marginal region and thus form a container which is filled with fresh dialysate. A hose element is usually welded to this container by which the dialysate can be removed from the bag. A connector is usually arranged at the hose element via which the dialysate container can be connected to the other fluid paths. The bag furthermore usually has a cut-out or eyelet at the side disposed opposite the hose and the bag can be hung onto a hook by it. It can hereby be ensured that the dialysate flows out of the bag without problem.

The dialysate usually comprises a buffer, an osmotic agent and electrolytes. Bicarbonate can e.g. be used as the buffer in this respect. Glucose is usually used as the osmotic agent. Alternatively, glucose polymers or glucose polymer derivates can also be used. The electrolytes usually include calcium and sodium.

The dialysate can be heat sterilized in this respect. This advantageously takes place after the dialysate has been filled into the bag. Both the dialysate and the bag are hereby heat sterilized. In this respect, the filled bag is usually first packed into an outer packaging, whereupon the total system is sterilized.

Since the finished dialysate solution can often not be heat sterilized or cannot be stored for a long time in dependence on the ingredients, provision can be made to store individual components of the dialysate separately and only to combine them shortly before the treatment. A first individual solution in this respect usually includes the buffer, while a second individual solution includes glucose and electrolytes. Optionally, more than two individual solutions, and thus more than two regions, can also be provided in a bag. In this respect, a multi-chamber bag, in particular a double-chamber bag, can be provided which has a plurality of separate regions for the storage of the individual solutions. These regions are separated by a connection element which can be opened mechanically to mix the individual fluids with one another. A so-called peel seam can in particular be provided between the two regions of the bag in this respect and opens on the application of a specific pressure to at least one of the regions of the bag.

Since relatively large quantities of dialysate are consumed during a night-time peritoneal dialysis treatment, a plurality of dialysate containers are usually used in parallel. They are connected to the fluid paths via corresponding connectors and can be used for the filling of the patient by a corresponding switching of the valves.

1.2 Drain

For the disposal of the consumed dialysis fluid, it can either be led off immediately into the drainage system or first be collected in a drain container. A bag is usually likewise used as a drain container in this respect. It is empty before the start of the treatment and can thus take up the consumed dialysate. The bag can then be correspondingly disposed of after the end of the treatment.

1.3 Cassette

As already initially described, the fluid system has a plurality of regions in which the dialysis machine has to have an effect on the fluid system. The fluid system has to be coupled to the dialysis machine for this purpose.

Cassettes are used to simplify the coupling of the fluid paths to the dialysis machine and the effect of the corresponding elements of the dialysis machine on the fluid paths. A plurality of regions in which the dialysis machine has an effect on the fluid paths are jointly arranged in such a cassette. For this purpose, a cassette usually has a hard part of plastic into which chambers open to one side are introduced as fluid paths. These chambers are covered by a flexible plastic film which provides the coupling to the dialysis machine. The flexible plastic film is in this respect usually welded to the hard part in a marginal region. The cassette is pressed with a coupling surface of the dialysis machine so that the actuators and/or sensors of the dialysis machine come into contact with corresponding regions of the cassette.

The cassette furthermore has connections for the connection of the dialysate container 10, of the connector 30 as well as of the drain 20.

A cassette in this respect usually includes at least one pump region and one or more valve regions. The fluid transport can thus be controlled by the fluid system via the cassette. The cassette can furthermore have sensor regions which enable a simple coupling of sensors of the dialysis machine to the fluid system. The cassette can optionally furthermore have one or more heating regions which can be coupled to corresponding heating elements of the dialysis machine.

Figure 4A:
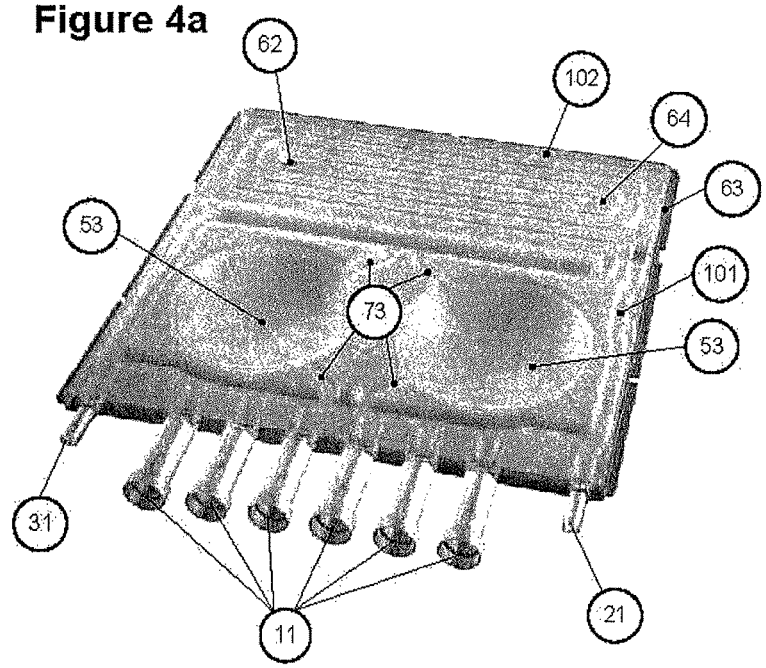
Figure 4B:
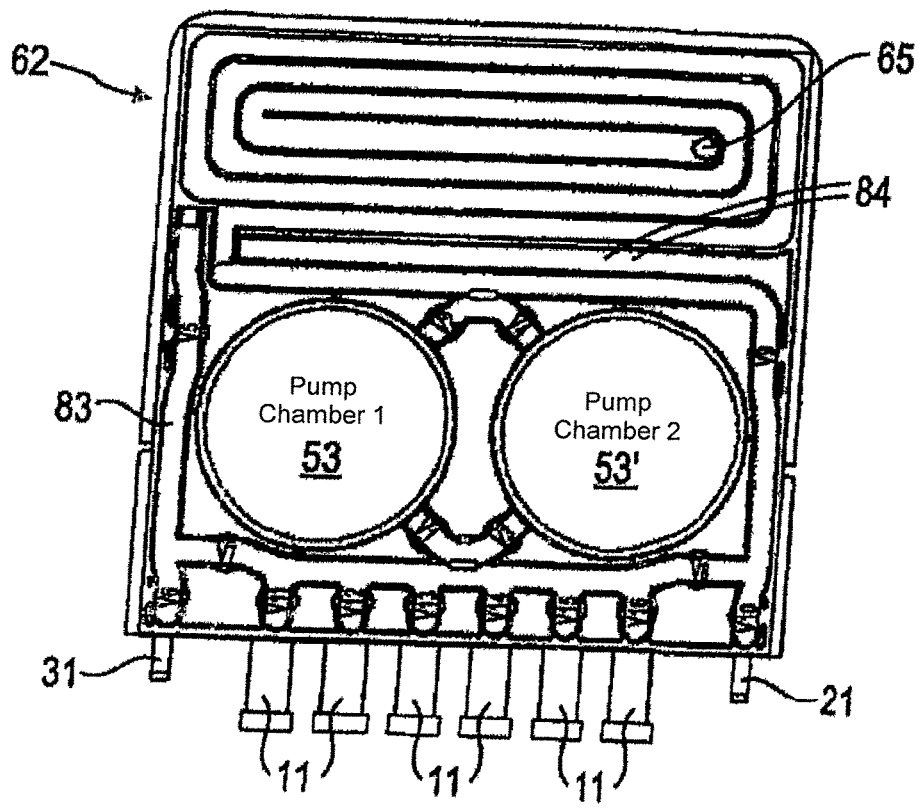

A first embodiment of a cassette is shown in FIGS. 4a and 4b. It has a hard part 101 of plastic in which the fluid paths and coupling regions are introduced as corresponding cut-outs, chambers and passages. The hard part can in this respect be produced e.g. as an injection molded part or as a deep drawn part. The coupling plane of the hard part 101 is covered by a flexible film 102 which is welded to the hard part in a marginal region. The flexible film 102 is pressed with the hard part by the pressing of the cassette with a coupling surface of the dialysis machine. The fluid paths within the cassette are separated from one another in a fluid tight manner by the pressing of the flexible film with the web regions of the hard part.

The cassette has connections for the connection of the cassette to the other fluid paths. On the one hand, a connection 21 is provided for the connection to the outflow 20 as well as a connection 31 for the connection to the connector 30. Corresponding hose elements which are not shown in FIG. 4a can be provided at these connections. The cassette furthermore has a plurality of connections 11 for the connection of dialysate containers 10. The connections 11 are in this respect designed in the first embodiment as connectors to which corresponding connector elements can be connected.

The connections are in each case in connection with fluid paths within the cassette. Valve regions are provided in these fluid paths. In these valve regions, the flexible film 102 can be pressed into the hard part 101 via valve actuators at the machine side such that the corresponding fluid path is blocked. The cassette in this respect first has a corresponding valve for each connection via which this connection can be opened or closed. The valve V10 is in this respect associated with the connection 21 for the outflow 20; the valve V6 is associated with the connection 31 for the patient connector 30. The valves V11 to V16 are associated with the connections 11 for the dialysate container 10.

Pump chambers 53 and 53' are furthermore provided in the cassette via which corresponding pump actuators of the dialysis machine can be actuated. The pump chambers 53 and 53' are in this respect concave cut-outs in the hard part 101 which are covered by the flexible film 102. The film can now be pressed into the pump chambers 53 and 53' or pulled out of these pump chambers again by pump actuators of the dialysis machine. A pumping flow through the cassette can hereby be generated in interaction with the valves V1 to V4 which switch the accesses and outlets of the pump chambers 53 and 53' and which were marked by the reference numerals 73 in FIG. 4a. The pump chambers can in this respect be connected via corresponding valve circuits to all connections of the cassette.

A heating region 62 is furthermore integrated into the cassette. In this region, the cassette is brought into contact with heating elements of the dialysis machine which heat the dialysate flowing through this region of the cassette. The heating region 62 in this respect has a passage for the dialysate which extends spirally over the heating region 62. The passage is in this respect formed by webs 64 of the hard part which are covered by the flexible film 102.

The heating region 62 is in this respect provided at both sides of the cassette. A flexible film is also arranged at the hard part in the heating region at the lower side 63 of the cassette for this purpose. The flexible film is in this respect also welded to the hard part in a marginal region. A passage is likewise arranged at the lower side and the dialysate flows through it. The passages on the lower side and on the upper side are in this respect formed by a middle plate of the hard part which separates the upper side from the lower side and on which webs are downwardly and upwardly provided which form the passage walls. In this respect, the dialysate first flows spirally on the upper side up to the aperture 65 through the middle plate from where the dialysate flows back at the lower side through the corresponding passage. The heating surface which is available for the heating of the fluid can be correspondingly enlarged by the heating region provided at the upper side and at the lower side. An embodiment of the cassette is, however, naturally also possible in which a heating region is only arranged on one side of the cassette.

Embodiments are the cassette are furthermore possible in which a heating element is integrated into the cassette. An electrical heating element such as a heating coil can in this respect in particular be cast into the hard part of the cassette. A heating element on the machine side can thus be dispensed with and the throughflow heating can be integrated into the cassette. In this respect, electrical contacts are arranged at the cassette for the connection of the electrical heating element.

The cassette furthermore has sensor regions 83 and 84 by which temperature sensors of the dialysis machine can be coupled to the cassette. The temperature sensors in this respect lie on the flexible film 102 and can thus measure the temperature of the fluid flowing through the passage disposed below. Two temperature sensors 84 are in this respect arranged at the inlet of the heating region. A temperature sensor 83 via which the temperature of the dialysate pumped to the patient can be measured is provided at the outlet at the patient side.

A second embodiment for a cassette is shown in FIG. 5. The cassette in this respect substantially corresponds in its design to the first embodiment, but does not include any heating region. On the use of this cassette, the heating therefore does not take place as shown in the first embodiment via a heating region integrated into the cassette, but rather e.g. via a heating bag which is placed onto a heating plate of the dialysis machine.

The second embodiment of a cassette shown in FIG. 5 in turn has fluid paths which can be opened and closed via valve regions which are here likewise numbered consecutively from V1 to V16. The cassette furthermore has connections for the connection to further components of the fluid system. In this respect, the connection 21 is in turn provided for the connection to the drain 20 and the connection 31 for connection to the connector 30 to the patient. Connections 11 are furthermore provided for the connection of dialysis containers 10.

Unlike the first embodiment, the cassette shown in the second embodiment has a further connection 66 for the connection of a heating bag. In this respect, the fluid can be pumped into a heating bag via the connection 66 for the heating of the fluid from the dialysate containers 10. This heating bag lies on a heating element so that the fluid present in the heating bag can be heated. The fluid is thereupon pumped from the heating bag 65 to the patient.

The pump chambers 53 and 53' and the valves V1 to V4 correspond in design and function to the corresponding components in the first embodiment.

Unlike the first embodiment, the cassette in the second embodiment does not have any sensor region for the connection of a temperature sensor. It is rather arranged in the region of the heating elements. The cassette, however, has measurement regions 85 and 86 for the measurement of the pressure in the pump chambers 53 and 53'. The measurement regions 85 and 86 are in this respect chambers which are in fluid communication with the pump chambers and are likewise covered by the flexible film. Pressure sensors at the apparatus side which measure the pressure in the measurement chambers 85 and 86 and thus in the pump chambers 53 and 53' can be coupled to the measurement regions.

The connection of the connections 11, 21, 31 and 66 of the cassette to the further components of the fluid system takes place via hose connections in the second embodiment. Connections are optionally arranged at the hose connections.

1.3 Hoses

The connection between the individual containers of the system, the cassette and the patient connector usually takes place via hose connections. Since they are in each case disposable articles, the hoses are in this respect usually already fixedly connected at at least one side to a further element. Hoses can e.g. already be provided at one or more of the connections of the cassette. Hoses can likewise already be in fixed communication with bags.

1.4 Connections

The fluid system is usually divided into a plurality of parts and packaged in sterile form in each case. These parts first have to be connected to one another for the treatment. The cassette and the dialysate bag or bags are in this respect in particular packaged separately from one another.

The connections between the individual elements of the fluid system usually takes place via connectors. The connectors are in this respect designed so that they enable a sterile connection between the individual components. This takes place e.g. via corresponding protective films which are automatically opened on the closing of the connector.

The connection of the individual components can in this respect take place manually by an operator or by the patient him or herself. Provision can alternatively be made that the connection of the individual components takes place by the dialysis machine.

For this purpose, the corresponding connectors can e.g. be placed into a connector receiver of the dialysis machine and can be automatically joined together by the dialysis machine.

An electronic control can furthermore be provided which monitors that the correct components of the system are connected to one another. Identification means such as barcodes or RFIDs which identify the components can be provided at the connectors for this purpose. The dialysis machine in this respect includes an identification means detection unit such as a barcode reader or an RFID detection unit which detects the identification means on the connectors. The controller of the peritoneal dialysis can hereby recognize whether the correct connectors were inserted.

Such a check of the correct assembly of the fluid system can in this respect in particular be combined with an automatic connection of the connectors. The system thus first checks whether the correct connectors were placed into the connector receivers. The connection between the connectors is only established by the dialysis machine when the correct connectors were inserted. Otherwise, the dialysis machine draws the attention of the user to the fact that the wrong connectors have been inserted.

2. The Dialysis Machine

The individual components of a dialysis machine will now be described in more detail in the following with reference to two embodiments.

A first embodiment of a dialysis machine is shown in this respect in FIG. 6 in which the first embodiment of a cassette is used. The peritoneal dialysis system resulting from the first embodiment of a dialysis machine and the first embodiment of a cassette is shown in FIG. 7 in this respect.

A second embodiment of a dialysis machine is shown in FIG. 8 in which the second embodiment of a cassette is used. The dialysis system resulting from the combination of the second embodiment of a dialysis machine and of the second embodiment of a cassette is then shown in FIG. 9.

The two embodiments differ in this respect, on the one hand, in the design of the heating, in the coupling between the dialysis machine and the cassette and in the design of the actuators and sensors.

2.1 Heating

The fresh dialysate has to be brought to body temperature before it is conveyed into the abdomen of the patient. The dialysis machine has a corresponding heating for this purpose.

The heating in this respect usually takes place via one or more heating elements. The heating elements can in this respect e.g. be ceramic heating elements. With such ceramic heating elements, a resistance strip is applied to a ceramic carrier. The heating strip is heated by the application of a voltage to it, whereby the ceramic carrier material is also heated. The ceramic heating element is in this respect usually arranged on a heating plate. It can be made of aluminum, for example. The fluid paths are in turn coupled to the heating plate so that the dialysate present in the fluid paths can be heated.

Two different embodiments are available for the heating of the fluid. On the one hand, a larger quantity of dialysate can first be heated which is only pumped to the patient after the heating phase. This usually takes place via a heating bag which is placed on a heating plate of the dialyzer.

The heating bag can in this respect be the dialysis bag in which the dialysate is provided. Usually, however, a separate heating bag is used in which the dialysate is pumped for heating. If the dialysate is heated in the heating bag, it is pumped to the patient from there.

Such a concept is realized in the second embodiment of a dialysis machine shown in FIGS. 8 and 9. In this respect, a heating bag 67 is provided which lies on a heating plate 68. The heating plate 68 is in this respect arranged on the upper side of the peritoneal dialyzer so that it is easily accessible. The heating bag 67 is in this respect connected to the cassette via a line 66'. The cassette in this respect has the valves V5, V9 and V15 via which the heating bag 67 can be connected to the other components of the fluid system. Fresh dialysate can thus be pumped from the dialysate containers 10 via the pump chambers to the heating bag 67. At the start of a treatment, the heating bag 67 is therefore first filled with cold dialysate. The dialysate in the heating bag 67 is then heated to body temperature via the heating plate 68. The dialysate is thereupon pumped to the patient via the pump chambers. The heating bag 67 can thereupon be filled again so that the dialysate quantity required for the next treatment cycle can be heated.

A temperature sensor 88, which is in contact with the heating bag 67 and can thus measure the temperature of the dialysate in the heating bag 67, is advantageously provided in the region of the heating plate 68 in this respect. A temperature sensor can furthermore be provided at the heating plate or at the heating element which measures the temperature of the heating element or of the heating plate. A corresponding controller now makes sure that the heating plate does not become too hot for the material of the bag.

The heating bag 67 can additionally take over functions in the balancing of the fluid flows. The heating plate 68 can thus be part of scales 87 via which the weight of the heating bag 67 can be determined. The fluid quantity which is supplied to the patient after heating can hereby be determined.

Alternatively to the heating of the dialysate via a heating bag shown in the second embodiment, the dialysate can also be heated while it is being pumped to the patient. The heating thus works in the form of a continuous-flow water heater which heats the dialysate moved through the fluid system while it is being pumped through the fluid paths.

In this concept, a dialysate passage is provided which is coupled to a heating element of the dialysis machine. While the dialysate flows through the dialysate passage, it takes up heat from the heating element of the dialysis machine while so doing.

Such a concept is implemented in the first embodiment of a dialysis machine which is shown in FIGS. 6 and 7. The heating region is integrated in the cassette in this respect, as was already shown above. On the coupling of the cassette to the dialysis machine, the heating region of the cassette comes thermally into contact with heating elements of the dialysis machine.

The heating elements can in this respect likewise be designed as ceramic heating elements and can be in contact with heating plates which are the coupled to the heating region of the cassette. As already shown with respect to the cassette, a respective heating plate which heats the dialysate flowing through the heating region is in this respect in contact both with the upper side and with the lower side of the heating region.

Respective temperature regions are provided in the cassette at the inflow and at the outflow of the heating region and come into contact with temperature sensors of the peritoneal dialysate by the coupling of the cassette. The temperature of the dialysate flowing into the heating region and the temperature of the dialysate flowing out of the heating region can thus be determined by the temperature sensors T1 to T3. Temperature sensors T4 and T5 are furthermore provided which determine the temperature of the heating elements and/or of the heating plates.

The use of at least two heating elements in this respect makes it possible to connect the heating elements to one another in each case such that they output substantially the same power at a supply voltage of 220 V as with a supply voltage of 110 V. For this purpose, the two heating elements are operated in a parallel circuit at 110 V, whereas they are operated in a series circuit at a supply voltage of 220V. Such an adaptation of the connection of the heating elements to the supply voltage can in this respect be implemented independently of whether the heating takes place in accordance with the first or the second embodiment.

2.2 Coupling the Cassette

To enable a coupling of the actuators and/or sensors of the dialysis machine to the corresponding regions of the cassette, the dialysis machine has a cassette receiver with a coupling surface to which the cassette can be coupled. The corresponding actuators, sensors and/or heating elements of the dialysis machine are arranged at the coupling surface.

The cassette is pressed with this coupling surface such that the corresponding actuators, sensors and/or heating elements come into contact with the corresponding regions in the cassette.

In this respect, a mat of a flexible material, in particular a silicone mat, is advantageously provided at the coupling surface of the dialysis machine. It ensures that the flexible film of the cassette is pressed with the web regions of the cassette and thus separates the fluid paths within the cassette.

A peripheral margin of the coupling surface is furthermore advantageously provided which is pressed with the marginal region of the cassette. The pressing in this respect advantageously takes place in an airtight manner so that an underpressure can be built up between the coupling surface and the cassette.

A vacuum system can optionally also be provided which can pump air out of the space between the coupling surface and the cassette. A particularly good coupling of the actuators, sensors and/or heating elements of the peritoneal dialysis device with the corresponding regions of the cassette is hereby made possible. In addition, the vacuum system allows a leak tightness check of the cassette. A corresponding vacuum is applied after the coupling for this purpose and a check is made whether this vacuum is maintained.

The pressing on of the cassette e.g. takes place pneumatically. For this purpose, usually an air cushion is provided which is filled with compressed air and thus presses the cassette onto the coupling surface.

The cassette receiver usually has a receiver surface which is disposed opposite the coupling surface and into which the hard part of the cassette is inserted. The receiver surface advantageously has corresponding recesses for this purpose. The receiver surface with the inserted cassette can then be pressed onto the coupling surface via a pneumatic pressing apparatus.

The insertion of the cassette can in this respect take place in different manners. In the first embodiment of a dialysis machine which is shown in FIG. 6, a drawer 111 is provided for this purpose which can be moved out of the dialysis machine. The cassette is inserted into this drawer. The cassette is then pushed into the dialysis machine together with the drawer. The pressing of the cassette with the coupling surface which is arranged in the interior of the apparatus thereupon takes place. In this respect, the cassette and the coupling surface are first moved mechanically toward one another and then pressed with one another pneumatically.

The coupling of a cassette 110 in accordance with the second embodiment is shown in more detail in FIG. 10. The coupling surface 130 is freely accessible by opening a door 140 so that the cassette can be arranged at the correct position at the coupling surface 130. The coupling surface 130 is in this respect inclined rearwardly toward the vertical, which enables an easier coupling. The door 140 can now be closed so that a receiver surface at the door comes into contact with the rear side of the cassette. The pressing now takes place by an air cushion arranged at the door. In addition, a vacuum is applied between the coupling surface and the cassette 110.

The first embodiment of a dialysis machine furthermore has an apparatus for automatic connecting. A connector receiver 112 is provided for this purpose into which the connectors of the dialysate bag 10 are inserted. The connector receiver 112 then moves into the apparatus where a barcode reader is provided which reads the barcodes applied to the connectors. The apparatus can thus check whether the correct bags were inserted. If the correct bags are recognized, the connector receiver 112 moves in completely and so connects the connectors of the bag to the connections 11 of the cassette formed as connectors.

In the second embodiment, such an automatic connecting was, in contrast, dispensed with. Hose sections are therefore arranged at the connections 11 of the cassette and have to be manually connected to the corresponding bags via connectors.

2.3 Pump Actuators

The pumping of the fluid through the fluid system takes place in the embodiments by a membrane pump which is formed by the pump chambers 53 and 53 together with the flexible film of the cassette. If the flexible film is in this respect pressed into the pump chamber by a corresponding pump actuator, fluid is pumped out of the pump chamber into the opened regions of the fluid paths of the cassette. Conversely, fluid is sucked out of the fluid paths into the pump chamber by pulling the film out of the pump chamber.

The pump stroke in this respect takes place by movement of a pump actuator into the pump chamber. The pump actuator is moved away from the pump chamber again for the suction stroke. An underpressure arises in this respect due to the airtight pressing of cassette and coupling surface by which the flexible film of the cassette follows the pump actuator and is thus pulled out of the pump chamber again.

To enable a good coupling of the pump actuator to the flexible film of the cassette, a vacuum system can moreover be provided. In this respect, in particular for force with which the flexible film is moved away from the pump chamber at a maximum during a suction stroke can be set via the setting of a corresponding vacuum between the coupling surface and the cassette.

The suction force of the pump can hereby be set very finely. The pump force is in contrast set by the thrust force of the actuator.

The balancing of the fluid flows can in this respect take place by the counting of the suction and pump strokes since the membrane pump has a high precision of the fluid quantity pumped with each stroke.

2.3.1. Hydraulic Drive

The structure of a first embodiment of a pump actuator is shown in FIG. 11. The pump actuator is moved hydraulically in this respect. A membrane 59 is provided for this purpose which is placed at the flexible film of the cassette. The membrane 59 can in this respect be produced e.g. from silicone. A chamber 54 which can be filled with hydraulic fluid is provided behind the membrane 59. By application of an overpressure in the chamber 54, the membrane 59, and with it the flexible film, is pressed into the pump chamber 53 of the cassette. By application of an underpressure to the chamber 54, the membrane 59 is, in contrast, pulled into the chamber 54. Due to the underpressure between the flexible film and the membrane, the flexible film follows this movement so that the volume of the pump chamber 53 increases. The pump process with the pump stroke and the suction stroke is shown schematically in FIG. 12*b* in this respect.

A hydraulic pump 58 is provided for the operation of the pump hydraulic system. It has a cylinder in which a piston can be moved to and fro via a motor 57. The hydraulic fluid is hereby pressed into the chamber 54 or sucked out of it again via a corresponding connection line. A transducer 56 is provided at the hydraulic pump 58 in this respect and the movement of the piston can be recorded via it. It can hereby be determined how much hydraulic fluid was pressed into the chamber 54 and how much hydraulic fluid was removed from it. Pressure sensors 55 are furthermore provided at the hydraulic system which measure the pressure in the hydraulic system. They on the one hand allow a functional check of the hydraulic system since the data of the pressure sensors can be compared with those of the transducer 56 and the leak tightness of the hydraulic system can hereby be checked.

In addition, the pressure sensors allow a determination of the pressure in the pump chamber 53 of the cassette. If the hydraulic pump 58 is not moved, a pressure balance is adopted between the chamber 54 and the pump chamber 53. The pressure of the hydraulic fluid thus corresponds to the pressure in the pump chamber 53.

Figure 12A:
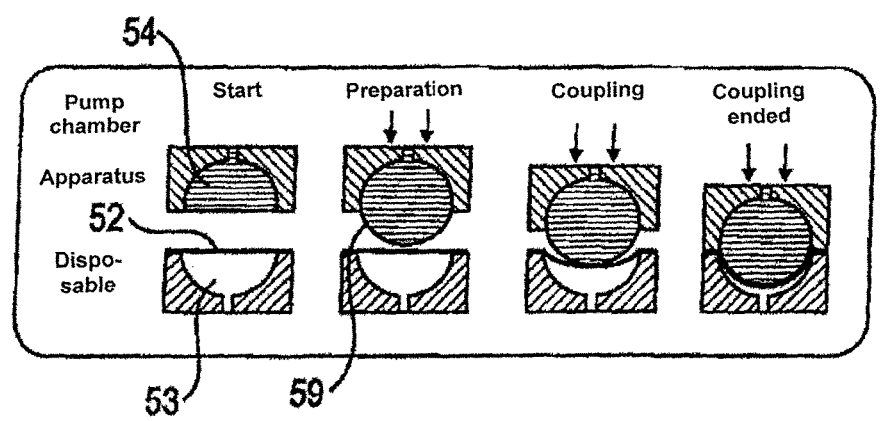
Figure 12B:
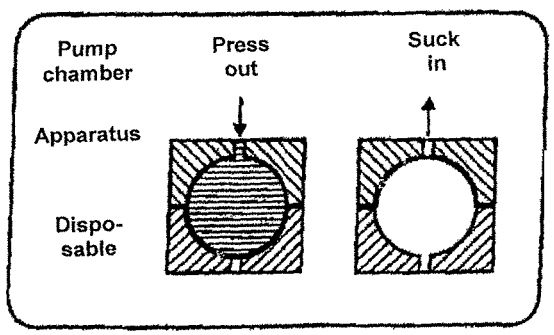

The coupling procedure of the pump actuator to the pump chamber 53 is now shown in FIG. 12a. In this respect, the chamber 54 is first loaded with hydraulic fluid such that the membrane 59 arches outwardly for the preparation of the coupling. The coupling surface and the cassette are thereupon moved toward one another so that the membrane 59 presses the flexible film of the cassette into the pump chamber 53. After the pressing of the coupling surface and of the cassette, the space between the membrane and the flexible film is outwardly closed in an airtight manner so that the flexible film follows the movement of the membrane. This is shown in FIG. 12b.

The pump actuator shown in FIG. 11 is in this respect implemented in the first embodiment of a dialysis machine, as can also be seen from FIG. 7. In this respect, a corresponding pump actuator is respectively provided for each of the two pump chambers 53 and 53'.

2.3.2 Electromechanical Drive

Alternatively, the pump actuator can also be operated in an electric motor manner. A correspondingly shaped ram is provided for this purpose which is pressed toward or away from the flexible film via an electric motor, in particular via a stepped motor, and the pump stroke or suction stroke is thus generated. Such pump actuators 151 and 152 are shown in the embodiment in FIG. 10. A vacuum system is in this respect advantageously provided which ensures that the flexible film also follows the ram in the suction movement.

2.4 Valve Actuators

A valve plunger can be provided as the valve actuator which presses the flexible film of the cassette into a corresponding chamber of the hard part and so closes the fluid passage in this region. The valve actuator can in this respect e.g. be pneumatically actuated. The plunger can in this respect be biased via a spring so that it either opens without pressure or closes without pressure.

Alternatively, the valve actuator can be implemented via a flexible membrane which is moved hydraulically or pneumatically. The flexible membrane is in this respect moved toward the cassette by application of pressure and so presses a corresponding valve region of the flexible film into a fluid passage to close it.

Valve actuators 71 which are coupled to the valve regions V1 to V16 of the cassette can be recognized in FIG. 10 on the coupling surface.

2.5 Sensors

The dialysis machine has sensors via which the machine can be controlled or its proper functioning can be monitored.

On the one hand, in this respect, one or more temperature sensors are provided via which the temperature of the dialysate and/or of the heating elements can be measured. In the first embodiment, the temperature sensors are in this respect arranged at the coupling surface to the cassette and can thus measure the temperature of the dialysate flowing through the cassette. In the second embodiment, in contrast, a temperature 88 is provided on the heating plate 68 which measures the temperature of the dialysate present in the bag 67. Temperature sensors can furthermore be provided at the heating element or elements.

One or more pressure sensors can furthermore be provided to determine the pressure in the pump chambers. It can hereby be prevented that dialysate is pumped to the patient at too high a pressure or that the suction pressure becomes too high on the sucking of dialysate from the patient.

In the first embodiment, the pressure measurement takes place in this respect via pressure sensors in the hydraulic system of the pump actuators, as was shown above. In the second embodiment, in contrast, pressure sensors 85' and 86' are provided in the coupling surface which directly measure the pressure in corresponding pressure measurement regions of the cassette. The coupling of these pressure sensors to the cassette is in this respect advantageously ensured by a vacuum system.

2.6 Input/Output Unit

The dialysis machine furthermore includes an input/output unit for communication with an operator. A corresponding display is in this respect provided for the output of information which can e.g. be implemented by light-emitting diodes, LCD displays or a screen. Corresponding input elements are provided for the inputting of commands. Push buttons and switches can e.g. be provided in this respect.

In both embodiments, a touch screen 120 is provided in this respect which allows an interactive menu navigation. Display elements 121 and 122 are furthermore provided which show states of the dialysis machine in compact form.

The first embodiment furthermore has a card reader 125 via which a patient card can be read. Data on the treatment of the respective patient can be stored on the patient card. The treatment procedure for the respective patient can hereby be individually fixed.

The peritoneal dialysis machine furthermore has an acoustic signal unit via which acoustic signals can be output. In this respect, an acoustic warning signal can in particular be output when an error state is registered. A loudspeaker is in this respect advantageously provided via which the acoustic signals can be generated.

2.7 Controller

The peritoneal dialysis machine furthermore has a controller by which all components can be controlled and monitored. The controller in this respect provides the automatic procedure of the treatment.

The basic structure of an embodiment of such a controller is now shown in FIG. 13.

The communication with the operator and with external information sources in this respect takes place via an interface computer 150. It communicates with a patient card reader 200, an input and output unit 210 which serves the communication with the patient and with a modem 220. Updated software can e.g. be uploaded via the modem 220.

The interface computer 150 is connected via an internal bus to an activity computer 160 and to a protective computer 170. The activity computer 160 and the protective computer 170 generate redundancy of the system. The activity computer 160 in this respect receives signals from the sensors of the system and calculates the control signals for the actuators 180. The protective computer 170 likewise receives signals from the sensors 180 and checks whether the commands output by the activity computer 160 are correct. If the protective computer 170 determines an error, it initiates a corresponding emergency procedure. The protective computer 170 can in particular trigger an alarm signal in this respect. The protective computer 170 can furthermore close the access to the patient. A special valve is arranged at the output of the cassette at the patient side for this purpose and only the protective computer 170 has access to it. This safety vale is in this respect closed in the pressureless state so that it closes automatically on a failure of the pneumatic system.

The protective computer 170 is furthermore connected to the barcode reader 190 and so checks the connection of the correct dialysis bag.

A diagnosis system 230 is furthermore provided via which errors of the system can be determined and remedied.

3. Implementation of the Invention

An embodiment of the present invention which is used in a dialysis system shown above or in one of the dialysis machines shown above will now be presented in the following. In this respect, the embodiment of the present invention can be combined with individual components or a plurality of components, such as were described above.

The dialysis machine has a setting means by means of which at least one treatment parameter can automatically be set dynamically and during the treatment operation of the dialysis machine.

In this respect, the setting means has both a time management element, also called a time manager, and a volume manager element, also called a volume manager. The setting means is advantageously a component of the above-described dialysis machine.

The time manager evaluates whether the treatment duration has to be shortened by a fixed factor (e.g. 10%) before each dwell phase. Since the treatment phases which were carried out are noted or are logged at the machine side, an evaluation can be made before each dwell phase whether the instantaneous time plan of the treatment is being adhered to.

If a delay is recognized at the machine side, the time difference between the planned and the actual treatment duration is first determined. This time difference (treatment delay) is deducted from the prescribed dwell phase duration if it does not exceed a fixed shortening time (e.g. delay<10% of the dwell phase duration). An exceeding of the maximum allowed time for shortening a dwell time has the consequence that the dwell phase is shortened by precisely this maximum fixed time.

This can be explained with reference to a first example. A dwell time of 100 minutes should accordingly take place. The instantaneous treatment delay in this case already amount to 5 minutes. The dwell time is consequently shortened to 95 minutes. This corresponds to a percentage shortening of 5%. Since the percentage shortening is below the percentage factor of 10%, an adaptation of the dwell phase duration to 95 minutes takes place by means of the setting means.

A still further example should be provided for explanation. A dwell time of 100 minutes should accordingly take place. The instantaneous treatment delay is here already 20 minutes. The treatment delay accordingly already amounts to 20% relative to the dwell phase duration. Since the percentage shortening will exceed the percentage factor by 10%, the dwell phase duration is fixed on the part of the setting means using the limiting means to 90 minutes (90% of the prescribed dwell phase duration, with the shortening corresponding to 10% of the dwell phase duration).

The volume manager evaluates whether the installation volume has to be shortened by a fixed factor (e.g. 10%) before each instillation. Since a log is permanently kept of the instantaneously available instillation volume and of the remaining treatment phases or treatment cycles to be run through on the part of the dialysis machine, an evaluation can be made before each instillation whether a specific solution type is present in sufficient quantity or with a sufficient volume for the carrying out of the following instillation phases.

If the instillation volume of the solution is not sufficient to carry out the treatment as prescribed, a shortening of all still outstanding and planned instillation volumes advantageously takes place, with first the lacking volume being determined.

For this purpose, in a first step, the lacking volume is deducted from the prescribed instillation volume of this instillation phase. If the lacking instillation volume falls below the fixed minimum factor (e.g. <10%), this volume is deducted from the instillation. An exceeding of the percentage factor has the consequence that the instillation is shortened by precisely this percentage factor.

This should be illustrated in more detail with reference to a first and second example.

In accordance with the first example, an instillation of 100 ml should take place. 2000 ml of a solution are required here for carrying out the further treatment. However, only 1980 ml are still available. The lacking volume thus amounts to 20 ml. The instillation is now reduced to 980 ml (=1000 ml−20 ml). This corresponds to a percentage shortening of 2%. Since the percentage shortening falls below the percentage factor (10%), it is caused at the machine side that 980 ml are instilled.

In accordance with the second example, an instillation of 1000 ml should take place. 2000 ml of a solution are also required here for carrying out the further treatment. However, only 1800 ml are still available. The lacking volume thus amounts to 200 ml. The instillation is now reduced to 800 ml (=1000 ml−200 ml). This corresponds to a percentage shortening of 20%. Since the percentage shortening exceeds the percentage factor of 10%, it is caused at the machine side that 900 ml are instilled, which corresponds to 90% of the prescribed instillation volume or a reduction by 10%.

REFERENCE NUMERAL LIST

Treatment cycles 1
Instillation phase 2
Base instillation phase 2'
Dwell phase 3
Drain phase 4
Base drain phase 4'
Initial drain 5
Drain phase 5'
Last instillation 6
Instillation phase 6'
Base cycle 7
Tidal cycles 8
Night 9
Container 10
Connection 11 for the connection of containers 10
Drain 20
Connections 21 for connection to the drain 20
Connector 30
Connection 31 for connection to the connector 30
Dialysis machine 40
Pump 50
Pump actuators 51
Pump region 52
Pump chambers 53 and 53'
(Hydraulic) chamber 54
Pressure sensors 55
Transducer 56

Motor 57
Hydraulic pump 58
Membrane 59
Heating 60
Heating element 61
Heating region 62
Lower side of the heating region 63
Webs 64
Opening 65
Connection 66 for a heating bag 67
Line 66'
Heating bag 67
Hot plate 68
Valves 70
Valve actuators 71
Valve regions 72
Valve regions 73 for the pump chambers
Valve regions V1 to V16
Sensors 80
Sensors 81
Sensor regions 82
Sensors regions 83 and 84 of the temperature sensors
Sensors regions 85 and 86 of the pressure sensors
Pressure sensors 85' and 86'
Scales 87
Temperature sensor 88
Temperature sensors T1 to T3
Temperature sensors T4 and T5
Controller 90
Balance 95
Fluid paths 100
Hard part 101
Flexible film 102
Cassette 110
Drawer 111
Connector receiver 112
Touch screen 120
Display elements 121 and 122
Card reader 125
Coupling surface 130
Door 140
Pump actuators 151 and 152
Interface computer 150
Activity computer 160
Protective computer 170
Actuators and sensors 180
Barcode reader 190
Patient card reader 200
Input and output unit 210
Modem 220
Diagnosis system 230

The invention claimed is:

1. A peritoneal dialysis machine for performing a treatment operation by which a patient connected to the dialysis machine undergoes peritoneal dialysis of multiple cycles of consecutive installation, dwell, and drain phases per cycle, the peritoneal dialysis machine operable in accordance with predefined and/or inputtable treatment parameters and comprising at least one manager selected from the group consisting of a time manager for managing dwell time and a volume manager for managing instillation volume,
wherein the time manager is configured to determine at least once during the treatment operation of the dialysis machine after at least one treatment cycle has been completed a time difference between a planned and an actual treatment duration, wherein the actual treatment duration comprises at least a time span starting from the beginning of an instillation phase of a first cycle up to a current point in time, wherein the time manager is configured to dynamically adapt the dwell time of at least one remaining dwell phases of the treatment operation on the basis of the time difference, and
wherein the volume manager is configured to store, before the start of a treatment, a treatment plan comprising a planned number of cycles to be performed for the treatment and planned instillation volumes to be instilled during the cycles, and to determine at least once during the treatment operation of the dialysis machine after at least one treatment cycle has been completed whether a volume of dialysis solution still available at a current point in time is sufficient for carrying out a remainder of the planned number of cycles in the stored treatment plan, wherein the volume manager is configured to dynamically adapt the instillation volume of at least one remaining instillation phase of the treatment operation on the basis of the determination.

2. A dialysis machine in accordance with claim 1, wherein the time manager and/or the volume manager is configured to determine whether an actual course of treatment corresponds to or differs from a planned course of treatment.

3. A dialysis machine in accordance with claim 1, characterized in that the time manager is configured to evaluate before each dwell phase whether there is a deviation from a time plan of the treatment, and the time manager is configured to adapt at least a dwell time of a following dwell phase if there is a deviation.

4. A dialysis machine in accordance with claim 1, characterized in that is adapted so that planned treatment duration can be adhered to.

5. A dialysis machine in accordance with claim 1, characterized in that a maximum possible adaption of the dwell time is limited to a predefined percentage factor of a planned dwell time.

6. A dialysis machine in accordance with claim 1, characterized in that for adapting the dwell time, the time difference determined by the time manager is deducted by the time manager from a predefined dwell time.

7. A dialysis machine in accordance with claim 1, characterized in that the volume manager is configured to evaluate before each dwell phase whether there is sufficient volume of dialysis fluid for all the remaining instillation phases of the treatment operation and planned instillation volumes, and the volume manager is configured to adapt at least an instillation volume of at least one following instillation phase if there is a deviation.

8. A dialysis machine in accordance with claim 7, characterized in that the volume manager is configured to adapt an instillation volume of a plurality of following instillation phases if there is a deviation.

9. A dialysis machine in accordance with claim 8, characterized in that the volume manager is configured to determine at least once during the treatment operation of the dialysis machine after at least one treatment cycle has been completed a volume difference between the available dialysis volume and a required dialysis volume, and the volume manager is configured to adapt the dwell volume by deducting the volume difference from a predefined instillation volume.

10. A dialysis machine in accordance with claim 1, characterized in that a maximum possible reduction of a planned instillation volume is limited to a percentage factor of the planned instillation volume.

11. A dialysis machine in accordance with claim 1, characterized in that the time manager is configured to automatically determine the time difference, or the volume manager is configured to automatically determine whether an available volume of the dialysis solution is sufficient for carrying out the remainder of the prescribed treatment.

12. A dialysis machine in accordance with claim 1, wherein the volume manager is configured to determine an available minimum hag volume of all connected instillation solution bags before the start of the treatment, the available minimum bag volume being the sum of a nominal volume and a guaranteed overfill volume of each bag.

13. A dialysis machine in accordance with claim 12, wherein the volume of dialysis solution still available at the current point in time is determined by the volume manager taking into account a nominal value and an overfill volume of connected instillation solution bags, and the machine's own consumption.

14. A dialysis machine in accordance with claim 1, wherein the volume manager is configured to take into account an overfill volume of connected instillation solution bags and the machine's own consumption.

15. A dialysis machine in accordance with claim 1, wherein the volume manager is configured such that an overfill volume of connected instillation solution bags is used for the machine's own fluid consumption and an adaptation takes place when the overfill volume is not sufficient for the machine's own consumption.

16. A method of operating a peritoneal dialysis machine in accordance with predefined and/or inputtable treatment parameters and comprising the steps of:
   subjecting a patient to a planned peritoneal dialysis treatment of multiple cycles of consecutive instillation, dwell, and drain phases per cycle,
   determining at least once during the dialysis treatment after at least one treatment cycle has been completed a time difference between a planned and an actual treatment duration, wherein the actual treatment duration comprises at least a time span starting from the beginning of an instillation phase of a first cycle up to a current point in time and
   dynamically adapting the dwell time of at least one remaining dwell phase of the treatment operation on the basis of the time difference.

17. A method of operating a peritoneal dialysis machine in accordance with predefined and/or imputable treatment parameters and comprising the steps of:
   subjecting a patient to a prescribed peritoneal dialysis treatment of multiple planned cycles of consecutive instillation, dwell, and drain phases per cycle,
   determining at least once during the dialysis treatment after at least one treatment cycle has been completed whether a volume of dialysis solution still available at a current point in time is sufficient for carrying out the planned number of cycles in the prescribed treatment, and
   dynamically adapting the instillation volume of at least one remaining instillation phase of the treatment operation on the basis of the determination.

18. A method in accordance with claim 17, comprising the step of determining an available minimum bag volume of all connected instillation solution bags before the start of the treatment, the available minimum bag volume being the sum of a nominal volume and a guaranteed overfill volume of each bag.

19. A method in accordance with claim 18, comprising the step of determining the volume of the dialysis solution still available at the current point in time taking into account a nominal volume and an overfill volume of connected instillation solution bags, and the machine's own consumption.

20. A method in accordance with claim 17, wherein the determination step takes into account an overfill volume of connected instillation solution bags and the machine's own consumption.

21. A method in accordance with claim 17, wherein an overfill volume of connected instillation solution bags is used for the machine's own fluid consumption and an adaption takes place when the overfill volume is not sufficient for the machine's own consumption.

22. A peritoneal dialysis machine for performing a treatment operation by which a patient connected to the dialysis machine undergoes peritoneal dialysis of multiple cycles of consecutive instillation, dwell, and drain phases per cycle, the peritoneal dialysis machine operable in accordance with predefined and/or inputtable treatment parameters and comprising a volume manager for managing instillation volume,
   wherein the volume manager is configured to determine at least once during the treatment operation of the dialysis machine after at least a priming step has been completed a volume of dialysis solution still available at a current point in time taking into account the machines' own consumption, and to determine whether the volume of dialysis solution still available is sufficient for carrying out a remainder of a prescribed treatment, and
   wherein the volume manager is configured to dynamically adapt the installation volume of at least one remaining instillation phase of treatment operation on the basis of the determination.

23. A dialysis machine in accordance with claim 22, wherein the volume manager is configured to determine an available minimum bag volume of all connected instillation solution bags before the start of the treatment, the available minimum bag volume being the sum of a nominal volume and a guaranteed overfill volume of each bag.

24. A dialysis machine in accordance with claim 22, wherein the volume manager is configured to determine the volume of dialysis solution still available taking into account a nominal volume and an overfill volume of connected instillation solution bags, and the machine's own consumption.

25. A dialysis machine in accordance with claim 22, wherein the volume manger is configured such that an overfill volume of connected instillation solution bags is used for the machine's own fluid consumption and an adaptation takes place when the overfill volume is not sufficient for the machine's own consumption.

26. A dialysis machine in accordance with claim 22, characterized in that a maximum possible adaption of a planned instillation volume is limited to a percentage factor of the planned instillation volume.

* * * * *